(12) United States Patent
Tian et al.

(10) Patent No.: US 7,468,458 B2
(45) Date of Patent: *Dec. 23, 2008

(54) ACCELERANTS FOR THE MODIFICATION OF NON-NATURAL AMINO ACIDS AND NON-NATURAL AMINO ACID POLYPEPTIDES

(75) Inventors: Feng Tian, San Diego, CA (US); Zhenwei Miao, San Diego, CA (US)

(73) Assignee: Amerx, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/875,761

(22) Filed: Oct. 19, 2007

(65) Prior Publication Data

US 2008/0139793 A1 Jun. 12, 2008

Related U.S. Application Data

(63) Continuation of application No. PCT/US2006/043472, filed on Nov. 8, 2006.

(60) Provisional application No. 60/734,589, filed on Nov. 8, 2005.

(51) Int. Cl.
C07C 281/00 (2006.01)
C07C 307/00 (2006.01)
C07C 243/00 (2006.01)
C07C 257/00 (2006.01)
C07C 251/32 (2006.01)

(52) U.S. Cl. .................. 564/34; 564/81; 564/148; 564/226; 564/253; 564/310; 564/464; 560/159

(58) Field of Classification Search ............ None
See application file for complete search history.

(56) References Cited

U.S. PATENT DOCUMENTS

2008/0139793 A1 6/2008 Tian et al.
2008/0154058 A1 6/2008 Tian et al.

FOREIGN PATENT DOCUMENTS

WO WO-2006-069246 A2 6/2006

OTHER PUBLICATIONS

Database CASREACT on STN, Acc. No. 115:256602, Hartman et al., Synthetic Communications (1991), 21(20), p. 2103-2107 (reaction 2 of 6 abstract).*

Ligouri, A. et al., "N,O-Heterocycles. Part 18. Regiochemistry and Site Selec tivity of N-Alkylhydroxylamine Additon to 2,3-Diphenylcyclopropenone," J. Chem. Soc. Perkin Trans. 1:961-965 (1987).
March, J. *Advanced Organic Chemistry*, "Reactions, Mechanisms, and Structure" John Wiley & Sons, New York, 4th ed., 1992; pp. 904-907.
Stuber, W. et al., "Preparation and Evaluation of PEG-Bound Thrombin Inhibitors Based on 4-Amidinophenylalanine," Peptide Res. 8(2):78-85 (1995).
PCT/US06/043472 Search Report dated Feb. 6, 2008.
Chin, J. et al., "An Expanded Eukaryotic Genetic Code," Science 301:964-967 (2003).
Chin, J.W. et al., "Addition of a photocrosslinking amino acid to the genetic code of *Escherichia coli*," PNAS USA 99:11020-11024 (2002).
Chin, J.W., et al., "Addition of $p$-Azido-$_L$-phenylalanine to the Genetic Code of *Escherichia coli*," JACS 124:9026-9027 (2002).
Chin, J.W. and Schultz, P.G., "In Vivo Photocrosslinking with Unnatural Amino Acid Mutagenesis," Chem. Bio. Chem. 11:1135-1137 (2002).
Cordes, E. and Jencks, W., "Nucleophilic Catalysis of Semicarbazone Formation by Anilines," J. Am. Chem. Soc., 1962, 84, pp. 826-831, (1962).
Dougherty, "Unnatural Amino Acids as Probes of Protein Structure and Function," Curr. Op. Chem. Biol.1 4:645-652 (2000).
Harris, J.M., "Laboratory Synthesis of Polyethylene Glycol Derivatives," JMS-Rev. Macromol. Chem. Phys. C25(3):325-373 (1985).
Hartman, G., "A Convenient Synthesis of 4-Aminomethyl-L-Phenylalanine," Synth. Comm. 21(20):2103-2107 (1991).
Jencks, W., "General Acid-Base Catalysis of Complex Reactions in Water," Chemical Reviews, 1972, vol. 72, No. 6, pp. 705-718.
Uno et al., "Steroselective Antibody-Catalyzed Oxime Formation," J. Am. Chem. Soc., 1994, 116, pp. 1145-1146.
Wang, L. and Schultz, P.G., "Expanding the genetic code," Chem. Comm. 1:1-11 (2002).
Wong, S. and Wong, L.J.C., "Chemical crosslinking and the stabilization of proteins and enzymes," Enzyme Microb. Technol. 14:866-874 (1992).
Zalipsky, S., "Functionalized Poly9ethylene glycol) for Preparation of Biologically Relevant Conjugates," Bioconjugate Chem 6:150-165 (1995).

* cited by examiner

*Primary Examiner*—Brian J Davis
(74) *Attorney, Agent, or Firm*—Wilson Sonsini Goodrich & Rosati

(57) ABSTRACT

Disclosed herein are accelerants for the formation of oxime-containing compounds from the reaction of a carbonyl-containing compound and a hydroxylamine-containing compound. The oxime-containing compound, the carbonyl-containing compound and the hydroxylamine-containing compound can each be a non-natural amino acid or a non-natural amino acid polypeptide. Also disclosed is the use of such accelerants to form oxime-containing compounds, the resulting oxime-containing compounds, and reaction mixtures containing such accelerants.

26 Claims, 13 Drawing Sheets

| Time | Oxime Yield (%)* using Accelerants 1-8 (20 mM) | | | | | | | | |
|---|---|---|---|---|---|---|---|---|---|
| | None | 1 | 2 | 3 | 4 | 5 | 6 | 7 | 8 |
| 2h | 17 | 36 | 32 | 30 | 30 | 32 | 32 | 39 | 30 |
| 9h | 51 | 79 | 67 | 59 | 58 | 68 | 58 | 72 | 59 |

* Values calculated by HPLC using an oxime standard peak

ACCELERANTS FOR THE MODIFICATION OF NON-NATURAL AMINO ACIDS AND NON-NATURAL AMINO ACID POLYPEPTIDES

RELATED APPLICATIONS

This application claims benefit of U.S. Provisional Application No. 60/734,589, entitled "Accelerants for the modification of non-natural amino acids and non-natural amino acid polypeptides" filed on Nov. 8, 2005.

FIELD OF THE INVENTION

Accelerants for the modification of molecules containing a carbonyl moiety, including non-natural amino acids and agents containing a non-natural amino acids.

BACKGROUND OF THE INVENTION

The ability to incorporate non-genetically encoded amino acids (i.e., "non-natural amino acids") into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages with functional groups that can be incorporated onto non-natural amino acids.

Methods are now available to selectively introduce chemical functional groups that are not found in proteins, that are chemically inert to all of the functional groups found in the 20 common, genetically-encoded amino acids and that may be used to react efficiently and selectively with reagents comprising certain functional groups to form stable covalent linkages.

SUMMARY OF THE INVENTION

Described herein are methods, compositions, techniques and strategies comprising accelerants for the reaction of hydroxylamine-containing compounds with carbonyl-containing compounds. The accelerants find use in the synthesis of oxime-containing compounds. The accelerants, in some embodiments, form bonds with the carbonyl-containing compounds, and as such, these new compounds are more reactive with hydroxylamine-containing compounds. Described herein are chemical compounds that can modulate the reaction of hydroxylamine-containing compounds with carbonyl-containing compounds. Also described herein are chemical compounds that can lower the activation barrier for the reaction of hydroxylamine-containing compounds with carbonyl-containing compounds. Also described herein are chemical compounds that, when included in a reaction comprising hydroxylamine-containing compounds and carbonyl-containing compounds, increase the rate at which oxime-containing compounds are formed. The hydroxylamine-, carbonyl-, and oxime-containing compounds can include non-natural amino acids, non-natural amino acid polypeptides and modified non-natural amino acid polypeptides. The carbonyl-containing compounds include compounds comprising an aromatic ketone moiety. Such compounds comprising an aromatic ketone moiety include amino acids and polypeptides. By way of example only, para-acetylphenylalanine or pAcF, is an amino acid that comprises an aromatic ketone moiety.

In one aspect are compounds that accelerate (referred to herein as accelerants) the rate of reaction between hydroxylamine-containing compounds with carbonyl-containing compounds to form oxime-containing compounds. In one embodiment, the hydroxylamine-containing compound is a non-natural amino acid, non-natural amino acid polypeptide or a modified non-natural amino acid polypeptide, and the carbonyl-containing compound comprises a desired functionality. In a further embodiment, the resulting oxime-containing compound comprises one of the aforementioned desired groups (i.e., a desired functionality). In a related aspect are the use of such compounds to accelerate the rate of reaction between a hydroxylamine-containing moiety on a non-natural amino acid, non-natural amino acid polypeptide or a modified non-natural amino acid polypeptide with a carbonyl-containing compound comprising a desired group (i.e., a desired functionality) to form an oxime-containing non-natural amino acid, non-natural amino acid polypeptide or modified non-natural amino acid polypeptide comprising a desired group. In another related aspect are reaction mixtures containing an accelerant, a hydroxylamine-containing non-natural amino acid, non-natural amino acid polypeptide or modified non-natural amino acid polypeptide, and a carbonyl-containing compound comprising a desired group. In another related aspect are oxime-containing non-natural amino acids, non-natural amino acid polypeptides or modified non-natural amino acid polypeptides comprising a desired group, wherein such oxime-containing compounds are formed from the reaction of a hydroxylamine-containing non-natural amino acid, non-natural amino acid polypeptide or modified non-natural amino acid polypeptide with a carbonyl-containing compound comprising a desired group in the presence of an accelerant. In one embodiment, the carbonyl group is not an aldehyde.

In another embodiment, the carbonyl group is an aromatic ketone.

In another embodiment, the carbonyl-containing compound is a non-natural amino acid, non-natural amino acid polypeptide or a modified non-natural amino acid polypeptide, and the hydroxylamine-containing compound comprises a desired functionality. In a further embodiment, the oxime-containing compound comprises one of the aforementioned groups. In a related aspect are the use of such compounds to accelerate the rate of reaction between a carbonyl-containing moiety on a non-natural amino acid, non-natural amino acid polypeptide or a modified non-natural amino acid polypeptide with a hydroxylamine-containing compound comprising a desired group to form an oxime-containing non-natural amino acid, non-natural amino acid polypeptide or modified non-natural amino acid polypeptide comprising a desired group. In another related aspect are reaction mixtures containing an accelerant, a carbonyl-containing non-natural amino acid, non-natural amino acid polypeptide or modified non-natural amino acid polypeptide, and a hydroxylamine-containing compound comprising a desired group. In another related aspect are oxime-containing non-natural amino acids, non-natural amino acid polypeptides or modified non-natural amino acid polypeptides comprising a desired group, wherein such oxime-containing compounds are formed from the reaction of a carbonyl-containing non-natural amino acid, non-natural amino acid polypeptide or modified non-natural amino acid polypeptide with a hydroxylamine-containing compound comprising a desired group in the presence of an accelerant. In one embodiment, the carbonyl group is not an aldehyde. In another embodiment, the carbonyl group is an aromatic ketone.

In a further aspect are methods for optimizing the reaction of a carbonyl-containing compound and a hydroxylamine-containing compound to form an oxime-containing compound by selection of at least one appropriate accelerant. In one embodiment, such optimization comprises comparing the yield of the oxime-containing compound in the presence of different accelerants, different molar ratios of accelerants, or a combination of the foregoing. In a further embodiment the yield of the oxime-containing compound is monitored by chromatography. In another embodiment, such optimization comprises comparing the amount of side-products that result in the presence of different accelerants, different molar ratios of accelerants, or a combination of the foregoing. In a further embodiment the quantity of side products is monitored by chromatography. In further embodiments, such optimization includes changing additional reaction conditions, including by way of example only pH and temperature. In one embodiment, the carbonyl group is not an aldehyde. In another embodiment, the carbonyl group is an aromatic ketone.

In one aspect are non-natural amino acids based upon an oxime bond in which the oxime bond was formed in the presence of an accelerant described herein. In further or additional embodiments, the non-natural amino acid is incorporated into a polypeptide, that is, such embodiments are non-natural amino acid polypeptides. In further or additional embodiments, the non-natural amino acids are functionalized on their sidechains such that their reaction with a derivatizing molecule generates an oxime bond formed in the presence of an accelerant described herein. In further or additional embodiments are non-natural amino acid polypeptides that can react with a derivatizing molecule, formed in the presence of an accelerant described herein (although such a reaction may be less efficient in the absence of an accelerant described herein), to generate an oxime-containing non-natural amino acid polypeptide. In further or additional embodiments, the non-natural amino acids are selected from amino acids having carbonyl, dicarbonyl or hydroxylamine sidechains. In further or additional embodiments, the non-natural amino acids comprise carbonyl or dicarbonyl sidechains where the carbonyl or dicarbonyl is selected from a ketone or an aldehyde. In another embodiment are non-natural amino acids containing a functional group that is capable of forming an oxime upon treatment with an appropriately functionalized co-reactant in the presence of an accelerant described herein (although such a reaction may be less efficient in the absence of an accelerant described herein). In a further or additional embodiment, the non-natural amino acids resemble a natural amino acid in structure but contain one of the aforementioned functional groups. In another or further embodiment the non-natural amino acids resemble phenylalanine or tyrosine (aromatic amino acids); while in a separate embodiment, the non-natural amino acids resemble alanine and leucine (hydrophobic amino acids). In one embodiment, the non-natural amino acids have properties that are distinct from those of the natural amino acids. In one embodiment, such distinct properties are the chemical reactivity of the sidechain, in a further embodiment this distinct chemical reactivity permits the sidechain of the non-natural amino acid to undergo a reaction while being a unit of a polypeptide even though the sidechains of the naturally-occurring amino acid units in the same polypeptide do not undergo the aforementioned reaction. In a further embodiment, the sidechain of the non-natural amino acid has a chemistry orthogonal to those of the naturally-occurring amino acids. In a further embodiment, the sidechain of the non-natural amino acid comprises an electrophile-containing moiety; in a further embodiment, the electrophile-containing moiety on the sidechain of the non-natural amino acid can undergo nucleophilic attack to generate an oxime-derivatized protein in the presence of an accelerant described herein (although such a reaction may be less efficient in the absence of an accelerant described herein). In any of the aforementioned embodiments in this paragraph, the non-natural amino acid may exist as a separate molecule or may be incorporated into a polypeptide of any length; if the latter, then the polypeptide may further incorporate naturally-occurring or non-natural amino acids. In one embodiment, the carbonyl group is not an aldehyde. In another embodiment, the carbonyl group is an aromatic ketone.

In another aspect are hydroxylamine-substituted molecules for the production of derivatized non-natural amino acid polypeptides based upon an oxime bond in the presence of an accelerant described herein (although such a reaction may be less efficient in the absence of an accelerant described herein). In a further embodiment are hydroxylamine-substituted molecules used to derivatize carbonyl- or dicarbonyl-containing non-natural amino acid polypeptides via the formation of an oxime bond between the derivatizing molecule and the carbonyl- or dicarbonyl-containing non-natural amino acid polypeptide in the presence of an accelerant described herein (although such a reaction may be less efficient in the absence of an accelerant described herein). In further embodiments the aforementioned carbonyl- or dicarbonyl-containing non-natural amino acid polypeptides are keto-containing non-natural amino acid polypeptides. In further or additional embodiments, the carbonyl- or dicarbonyl-containing non-natural amino acids comprise sidechains selected from a ketone or an aldehyde. In further or additional embodiments, the hydroxylamine-substituted molecules comprise a desired functionality. In further or additional embodiments, the hydroxylamine-substituted molecules are hydroxylamine-substituted polyethylene glycol (PEG) molecules. In a further embodiment, the sidechain of the non-natural amino acid has a chemistry orthogonal to those of the naturally-occurring amino acids that allows the non-natural amino acid to react selectively with the hydroxylamine-substituted molecules in the presence of an accelerant described herein (although such a reaction may be less efficient in the absence of an accelerant described herein). In a further embodiment, the sidechain of the non-natural amino acid comprises an electrophile-containing moiety that reacts selectively with the hydroxylamine-containing molecule in the presence of an accelerant described herein (although such a reaction may be less efficient in the absence of an accelerant described herein); in a further embodiment, the electrophile-containing moiety on the sidechain of the non-natural amino acid can undergo nucleophilic attack to generate an oxime-derivatized protein in the presence of an accelerant described herein (although such a reaction may be less efficient in the absence of an accelerant described herein). In a further aspect related to the embodiments described in this paragraph are the modified non-natural amino acid polypeptides that result from the reaction of the derivatizing molecule with the non-natural amino acid polypeptides in the presence of an accelerant described herein (although such a reaction may be less efficient in the absence of an accelerant described herein). Further embodiments include any further modifications of the already modified non-natural amino acid polypeptides. In one embodiment, the carbonyl group is not an aldehyde. In another embodiment, the carbonyl group is an aromatic ketone.

In another aspect are carbonyl- or dicarbonyl-substituted molecules for the production of derivatized non-natural amino acid polypeptides based upon an oxime bond, wherein the oxime bond is formed in the presence of an accelerant described herein (although such a reaction may be less efficient in the absence of an accelerant described herein). In a further embodiment are carbonyl- or dicarbonyl-substituted molecules used to derivatize hydroxylamine-containing non-natural amino acid polypeptides via the formation of an oxime bond in the presence of an accelerant described herein (although such a reaction may be less efficient in the absence of an accelerant described herein). In a further embodiment the carbonyl- or dicarbonyl-substituted molecules are aldehyde-substituted molecules or ketone-substituted moieties. In further embodiments, the carbonyl- or dicarbonyl-substituted molecules comprise a desired functionality. In further or additional embodiments, the aldehyde-substituted molecules are aldehyde-substituted polyethylene glycol (PEG) molecules. In further or additional embodiments, the ketone-substituted molecules are ketone-substituted polyethylene glycol (PEG) molecules. In a further embodiment, the sidechain of the non-natural amino acid has a chemistry orthogonal to those of the naturally-occurring amino acids that allows the non-natural amino acid to react selectively with the carbonyl- or dicarbonyl-substituted molecules in the presence of an accelerant described herein (although such a reaction may be less efficient in the absence of an accelerant described herein). In a further embodiment, the sidechain of the non-natural amino acid comprises a moiety (e.g., hydroxylamine group) that reacts selectively with the carbonyl- or dicarbonyl-containing molecule in the presence of an accelerant described herein (although such a reaction may be less efficient in the absence of an accelerant described herein); in a further embodiment, the nucleophilic moiety on the sidechain of the non-natural amino acid can undergo electrophilic attack to generate an oxime-derivatized protein in the presence of an accelerant described herein (although such a reaction may be less efficient in the absence of an accelerant described herein). In a further aspect related to the embodiments described in this paragraph are the modified non-natural amino acid polypeptides that result from the reaction of the derivatizing molecule with the non-natural amino acid polypeptides in the presence of an accelerant described herein (although such a reaction may be less efficient in the absence of an accelerant described herein). Further embodiments include any further modifications of the already modified non-natural amino acid polypeptides. In one embodiment, the carbonyl group is not an aldehyde. In another embodiment, the carbonyl group is an aromatic ketone.

In another aspect are mono-, bi- and multi-functional linkers for the generation of derivatized non-natural amino acid polypeptides based upon an oxime bond, wherein the oxime bond is formed in the presence of an accelerant described herein (although such a reaction may be less efficient in the absence of an accelerant described herein). In one embodiment are molecular linkers (bi- and multi-functional) that can be used to connect carbonyl- or dicarbonyl-containing non-natural amino acid polypeptides to other molecules in the presence of an accelerant described herein (although such a reaction may be less efficient in the absence of an accelerant described herein). In another embodiment are molecular linkers (bi- and multi-functional) that can be used to connect hydroxylamine-containing non-natural amino acid polypeptides to other molecules in the presence of an accelerant described herein (although such a reaction may be less efficient in the absence of an accelerant described herein). In another embodiment the carbonyl- or dicarbonyl-containing non-natural amino acid polypeptides comprise a ketone and/or an aldehyde sidechain. In an embodiment utilizing a hydroxylamine-containing non-natural amino acid polypeptide, the molecular linker contains a carbonyl or dicarbonyl group at one of its termini; in further embodiments, the carbonyl or dicarbonyl group is selected from an aldehyde group or a ketone group. In further or additional embodiments, the hydroxylamine-substituted linker molecules are hydroxylamine-substituted polyethylene glycol (PEG) linker molecules. In further or additional embodiments, the carbonyl- or dicarbonyl-substituted linker molecules are carbonyl- or dicarbonyl-substituted polyethylene glycol (PEG) linker molecules. Throughout, the phrase "other molecules" includes, by way of example only, proteins, other polymers (branched and unbranched), small molecules, and groups also identified as a "desired functionality." In further or additional embodiments, the hydroxylamine-containing molecular linkers comprise the same or equivalent groups on all termini so that upon reaction with a carbonyl- or dicarbonyl-containing non-natural amino acid polypeptide in the presence of an accelerant described herein (although such a reaction may be less efficient in the absence of an accelerant described herein), the resulting product is the homo-multimerization of the carbonyl- or dicarbonyl-containing non-natural amino acid polypeptide. In further embodiments, the homo-multimerization is a homo-dimerization. In further or additional embodiments, the carbonyl- or dicarbonyl-containing molecular linkers comprise the same or equivalent groups on all termini so that upon reaction with a hydroxylamine-containing non-natural amino acid polypeptide in the presence of an accelerant described herein (although such a reaction may be less efficient in the absence of an accelerant described herein), the resulting product is the homo-multimerization of the hydroxylamine-containing non-natural amino acid polypeptide. In further embodiments, the homo-multimerization is a homo-dimerization. In a further embodiment, the sidechain of the non-natural amino acid has a chemistry orthogonal to those of the naturally-occurring amino acids that allows the non-natural amino acid to react selectively with the hydroxylamine-substituted linker molecules in the presence of an accelerant described herein (although such a reaction may be less efficient in the absence of an accelerant described herein). In a further embodiment the sidechain of the non-natural amino acid has a chemistry orthogonal to those of the naturally-occurring amino acids that allows the non-natural amino acid to react selectively with the carbonyl- or dicarbonyl-substituted linker molecules in the presence of an accelerant described herein (although such a reaction may be less efficient in the absence of an accelerant described herein). In a further embodiment the sidechain of the non-natural amino acid comprises an electrophile-containing moiety that reacts selectively with the hydroxylamine-containing linker molecule in the presence of an accelerant described herein (although such a reaction may be less efficient in the absence of an accelerant described herein); in a further embodiment, the electrophile-containing moiety on the sidechain of the non-natural amino acid can undergo nucleophilic attack by the hydroxylamine-containing linker molecule to generate an oxime-derivatized protein in the presence of an accelerant described herein (although such a reaction may be less efficient in the absence of an accelerant described herein). In a further aspect related to the embodiments described in this paragraph are the linked (modified) non-natural amino acid polypeptides that result from the reaction of the linker molecule with the non-natural amino acid polypeptides. Further embodiments include any further modifications of the already linked (modified) non-natural amino acid polypeptides. In one embodiment, the carbonyl group is not an aldehyde. In another embodiment, the carbonyl group is an aromatic ketone.

In one aspect are methods to derivatize proteins via the condensation of carbonyl or dicarbonyl and hydroxylamine reactants in the presence of an accelerant described herein (although such a reaction may be less efficient in the absence of an accelerant described herein) to generate an oxime-based product. Included within this aspect are methods for the derivatization of proteins based upon the condensation of carbonyl- or dicarbonyl- and hydroxylamine-containing reactants to generate an oxime-derivatized protein adduct. In additional or further embodiments are methods to derivatize keto-containing proteins with hydroxylamine-functionalized polyethylene glycol (PEG) molecules. In yet additional or further aspects, the hydroxylamine-substituted molecule can include proteins, other polymers (branched and unbranched), small molecules and groups also identified as a "desired functionality." In one embodiment, the carbonyl group is not an aldehyde. In another embodiment, the carbonyl group is an aromatic ketone.

In another aspect are methods for the chemical synthesis of hydroxylamine-substituted molecules for the derivatization of keto-substituted proteins in the presence of an accelerant described herein (although such a reaction may be less efficient in the absence of an accelerant described herein). In one embodiment, the hydroxylamine-substituted molecule can comprise peptides, other polymers (non-branched and branched) and small molecules. In one embodiment are methods for the preparation of hydroxylamine-substituted molecules suitable for the derivatization of carbonyl- or dicarbonyl-containing non-natural amino acid polypeptides in the presence of an accelerant described herein (although such a reaction may be less efficient in the absence of an accelerant described herein), including by way of example only, keto-containing non-natural amino acid polypeptides. In a further or additional embodiment, the non-natural amino acids are incorporated site-specifically during the in vivo translation of proteins. In a further or additional embodiment, the hydroxylamine-substituted molecules allow for the site-specific derivatization of this carbonyl- or dicarbonyl-containing non-natural amino acid via nucleophilic attack of the carbonyl or dicarbonyl group to form an oxime-derivatized polypeptide in a site-specific fashion, wherein the oxime-derivatized polypeptide is formed in the presence of an accelerant described herein (although such a reaction may be less efficient in the absence of an accelerant described herein). In a further or additional embodiment, the method for the preparation of hydroxylamine-substituted molecules provides access to a wide variety of site-specifically derivatized polypeptides. In a further or additional embodiment are methods for synthesizing hydroxylamine-functionalized polyethylene glycol (PEG) molecules.

In another aspect are methods for the chemical derivatization of carbonyl- or dicarbonyl-substituted non-natural amino acid polypeptides, in the presence of an accelerant described herein (although such a reaction may be less efficient in the absence of an accelerant described herein), using a hydroxylamine-containing bi-functional linker. In one embodiment are methods for attaching a hydroxylamine-substituted linker to a carbonyl- or dicarbonyl-substituted protein via a condensation reaction to generate an oxime bond in the presence of an accelerant described herein (although such a reaction may be less efficient in the absence of an accelerant described herein). In further or additional embodiments, the carbonyl- or dicarbonyl-substituted non-natural amino acid is a keto-substituted non-natural amino acid. In further or additional embodiments, the non-natural amino acid polypeptides are derivatized site-specifically and/or with precise control of three-dimensional structure, using a hydroxylamine-containing bi-functional linker. In one embodiment, such methods are used to attach molecular linkers (mono- bi- and multi-functional) to carbonyl- or dicarbonyl-containing (including by way of example keto-containing) non-natural amino acid polypeptides, wherein at least one of the linker termini contains a hydroxylamine group which can link to the carbonyl- or dicarbonyl-containing non-natural amino acid polypeptides via an oxime bond in the presence of an accelerant described herein (although such a reaction may be less efficient in the absence of an accelerant described herein). In a further or additional embodiment, these linkers are used to connect the carbonyl- or dicarbonyl-containing non-natural amino acid polypeptides to other molecules, including by way of example, proteins, other polymers (branched and non-branched), small molecules and groups also identified as a "desired functionality." In one embodiment, the carbonyl group is not an aldehyde. In another embodiment, the carbonyl group is an aromatic ketone.

In some embodiments, the non-natural amino acid polypeptide is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is identical to the first polypeptide, in other embodiments, the second polypeptide is a different polypeptide. In some embodiments, the non-natural amino acid polypeptide comprises at least two amino acids linked to a water soluble polymer comprising a poly(ethylene glycol) moiety.

In some embodiments, the non-natural amino acid polypeptide comprises a substitution, addition or deletion that increases affinity of the non-natural amino acid polypeptide for a receptor. In some embodiments, the non-natural amino acid polypeptide comprises a substitution, addition, or deletion that increases the stability of the non-natural amino acid polypeptide. In some embodiments, the non-natural amino acid polypeptide comprises a substitution, addition, or deletion that increases the aqueous solubility of the non-natural amino acid polypeptide. In some embodiments, the non-natural amino acid polypeptide comprises a substitution, addition, or deletion that increases the solubility of the non-natural amino acid polypeptide produced in a host cell. In some embodiments, the non-natural amino acid polypeptide comprises a substitution, addition, or deletion that modulates protease resistance, serum half-life, immunogenicity, and/or expression relative to the amino-acid polypeptide without the substitution, addition or deletion.

In some embodiments, the non-natural amino acid polypeptide is an agonist, partial agonist, antagonist, partial antagonist, or inverse agonist. In some embodiments, the agonist, partial agonist, antagonist, partial antagonist, or inverse agonist comprises a non-natural amino acid is linked to a water soluble polymer. In some embodiments, the water polymer comprises a poly(ethylene glycol) moiety. In some embodiments, the polypeptide comprising a non-natural amino acid linked to a water soluble polymer prevents dimerization of the corresponding receptor. In some embodiments, the polypeptide comprising a non-natural amino acid linked to a water soluble polymer modulates binding of the polypeptide to a binding partner. In some embodiments, the polypeptide comprising a non-natural amino acid linked to a water soluble polymer modulates one or more properties or activities of the polypeptide.

Also described herein are methods of making a non-natural amino acid polypeptide linked to a water soluble polymer. In some embodiments, the method comprises contacting an isolated polypeptide comprising a non-natural amino acid with a water soluble polymer comprising a moiety that reacts with the non-natural amino acid in the presence of an accelerant described herein (although such a reaction may be less efficient in the absence of an accelerant described herein). In some embodiments, the non-natural amino acid incorporated into is reactive toward a water soluble polymer that is otherwise unreactive toward any of the 20 common amino acids. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

Also described herein are compositions comprising a polypeptide comprising at least one of the non-natural amino acids described herein and a pharmaceutically acceptable carrier. In some embodiments, the non-natural amino acid is linked to a water soluble polymer. Also described herein are pharmaceutical compositions comprising a pharmaceutically acceptable carrier and a polypeptide, wherein at least one amino acid is substituted by a non-natural amino acid. In some embodiments, the non-natural amino acid comprises a saccharide moiety. In some embodiments, the water soluble polymer is linked to the polypeptide via a saccharide moiety. Also described herein are prodrugs of the non-natural amino acids, non-natural amino acid polypeptides, and modified non-natural amino acid polypeptides; further described herein are compositions comprising such prodrugs and a pharmaceutically acceptable carrier. Also described herein are metabolites of the non-natural amino acids, non-natural amino acid polypeptides, and modified non-natural amino acid polypeptides; such metabolites may have a desired activity that complements or synergizes with the acidity of the non-natural amino acids, non-natural amino acid polypeptides, and modified non-natural amino acid polypeptides. Also described herein are the use of the non-natural amino acids, non-natural amino acid polypeptides, and modified non-natural amino acid polypeptides described herein to provide a desired metabolite to an organism, including a patient in need of such metabolite.

Also described herein are libraries of the non-natural amino acids described herein or libraries of the non-natural amino acid polypeptides described herein, or libraries of the modified non-natural amino acid polypeptides described herein, or combination libraries thereof, wherein the members of the library comprise on oxime-linkage formed in the presence of an accelerant described herein (although such a reaction may be less efficient in the absence of an accelerant described herein).

Also described herein are methods for screening libraries described herein for a desired activity, or for using the arrays to screen the libraries described herein, or for other libraries of compounds and/or polypeptides and/or polynucleotides for a desired activity. Also described herein is the use of such activity data from library screening to develop and discover new therapeutic agents, as well as therapeutic agents themselves.

Also described herein are methods for accelerating the conjugation of small molecules, including by way of example the conjugation of a hydroxylamine group on one reagent with a carbonyl group on another reagent, wherein neither reagent is a non-natural amino acid. In other words, the use of accelerants described herein is not limited to the further functionalization of non-natural amino acids and non-natural amino acid polypeptides, but can also be used to facilitate the formation of oxime bonds between any two reagents. By way of example only, this embodiment includes the use of accelerants in the formation/building of dynamic libraries from hydroxylamine-containing reagents and carbonyl-containing reagents. Of course, such dynamic libraries can include non-natural amino acids, but such dynamic libraries are not limited to the inclusion of non-natural amino acids.

Also described herein are methods of increasing therapeutic half-life, serum half-life or circulation time of a polypeptide that comprise substituting a non-natural amino acid for any one or more amino acids in a naturally occurring polypeptide, and/or adding a non-natural amino acid into a naturally occurring polypeptide, and/or linking the polypeptide to a water soluble polymer via an oxime bond formed in the presence of an accelerant described herein (although such a reaction may be less efficient in the absence of an accelerant described herein).

Also described herein are methods of treating a patient in need of such treatment with an effective amount of a pharmaceutical composition comprising a polypeptide comprising a non-natural amino acid comprising an oxime bond formed in the presence of an accelerant described herein (although such a reaction may be less efficient in the absence of an accelerant described herein) and a pharmaceutically acceptable carrier. In some embodiments, the non-natural amino acid is linked to a water soluble polymer.

In any of the aforementioned aspects or embodiments, the use of an accelerant includes the use of a single accelerant or multiple accelerants. Further, in any of the aforementioned aspects or embodiments the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, in any of the aforementioned aspects or embodiments the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, in any of the aforementioned aspects or embodiments the accelerant includes compounds that can be substantially removed in vacuo from the resulting oxime-containing compound. Further, in any of the aforementioned aspects or embodiments the accelerant includes compounds containing an amine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

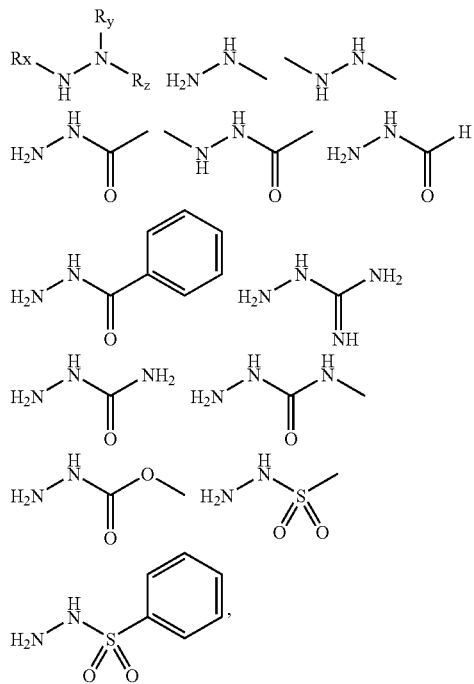

wherein $R_x$, $R_y$, and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

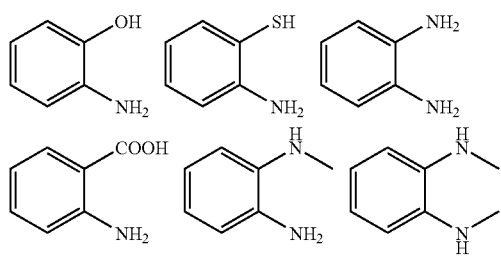

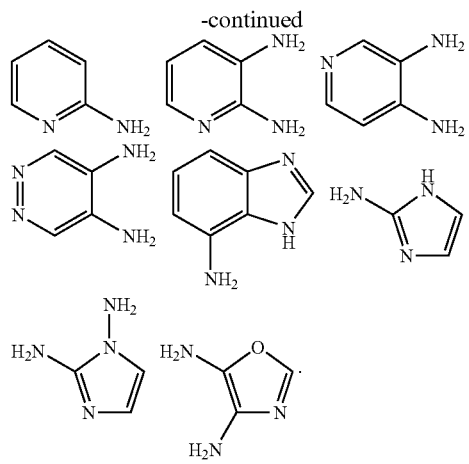

In a further embodiment, the accelerant is an oxoamine derivative. In a further embodiment, the oxoamine derivative is selected from the group:

Oxoamine Derivatives:

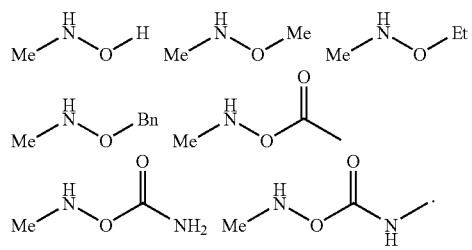

In a further embodiment, the accelerant include compounds selected from the group consisting of:

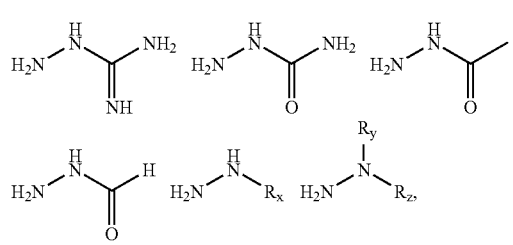

wherein $R_x$, $R_y$ and $R_z$ are selected from the group consisting of: $L_x$-H, $L_x$-alkyl, $L_x$-aryl $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10; between about 2.0 and 9.0; between about 2.0 and 8.0; between about 3.0 and 7.0; between about 4.0 and 6.0; between 3.0 and 10.0; between about 4.0 and 10.0; between about 3.0 and 9.0; between about 3.0 and 8.0; between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0. Note however, for any pH ranges described herein, the phrase "between about" in reference to a low and high pH value means that the "about" applies to both the low and the high pH value; by way of example only, "between about 3.0 and 10.0" is equivalent to "between about 3.0 and about 10.0." Furthermore, unless stated otherwise, for any range presented herein, in which "about" is presented before a lower limit and not before an upper limit (or in the case where "about" is placed before an upper limit and not a lower limit), then that is understood to mean that the word "about" appears before both limits of the range.

Further, in any of the aforementioned aspects or embodiments, the term "accelerant" includes a compound having a least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime-containing compound, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In a further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$— and —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include but are not limited to various water soluble polymers, peptides or proteins such as serum albumin, or other moieties that increase serum half-life of peptides.

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like (Maynard & Georgiou, 2000, *Annu. Rev. Biomed. Eng.* 2:339-76; Hudson, 1998, *Curr. Opin. Biotechnol.* 9:395-402). Another functional substructure is a single chain Fv (scFv), comprised of the variable regions of the immunoglobulin heavy and light chain, covalently connected by a peptide linker (S-z Hu et al., 1996, *Cancer Research*, 56, 3055-3061). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments."

The term "aryl" means, unless otherwise stated, a polyunsaturated, aromatic, hydrocarbon substituent which can be a single ring or multiple rings (including but not limited to from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, aralkyl) includes both aryl and heteroaryl rings as defined above. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789; all of which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to a compound and molecules it binds to or the compound.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

"Cofolding," as used herein, refers specifically to refolding processes, reactions, or methods which employ at least two polypeptides which interact with each other and result in the transformation of unfolded or improperly folded polypeptides to native, properly folded polypeptides.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, less than about 0.01, and in another embodiment less than about 0.001.

The term "conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the methods and compositions described herein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins:Structures and Molecular Properties* (W H Freeman & Co.; 2nd edition (December 1993)

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the methods and compositions described herein may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "desired functionality," as used herein refers to any one or all of the following groups: a label; a dye; a polymer; a water-soluble polymer; a derivative of polyethylene glycol; a photocrosslinker; a cytotoxic compound; a drug; an affinity label; a radionuclide; a derivative of biotin; a quantum dot; a nanotransmitter; a radiotransmitter; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid, and any combination of the above.

The term "dicarbonyl" as used herein refers to a group containing at least two moieties selected from the group consisting of —C(O)—, —S(O)—, —S(O)$_2$—, and —C(S)—, including, but not limited to, 1,2-dicarbonyl groups, a 1,3-dicarbonyl groups, and 1,4-dicarbonyl groups, and groups containing a least one ketone group, and/or at least one aldehyde groups, and/or at least one ester group, and/or at least one carboxylic acid group, and/or at least one thioester group. Such dicarbonyl groups include diketones, ketoaldehydes, ketoacids, ketoesters, and ketothioesters. In addition, such groups may be part of linear, branched, or cyclic molecules. The two moieties in the dicarbonyl group may be the same or different, and may include substituents that would produce, by way of example only, an ester, a ketone, an aldehyde, a thioester, or an amide, at either of the two moieties.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in degree, amount, potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "halogen" includes fluorine, chlorine, iodine, and bromine.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "linkage" or "linker" is used herein to refer to groups or bonds that normally are formed as the result of a chemical reaction and typically are covalent linkages or bonds (the process of creating such a linkage or linker is referred to herein as linking/linked or coupling/coupled, as well as other synonyms recognized by those in the art). Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the polypeptide has been secreted, including medium either before or after a proliferation step. The term also may encompass buffers or reagents that contain host cell lysates, such as in the case where the polypeptide is produced intracellularly and the host cells are lysed or disrupted to release the polypeptide.

A "metabolite" of a (modified) non-natural amino acid polypeptide disclosed herein is a derivative of that (modified) non-natural amino acid polypeptide that is formed when the (modified) non-natural amino acid polypeptide is metabolized. The term "active metabolite" refers to a biologically active derivative of a (modified) non-natural amino acid polypeptide that is formed when the (modified) non-natural amino acid polypeptide is metabolized. The term "metabolized" refers to the sum of the processes (including, but not limited to, hydrolysis reactions and reactions catalyzed by enzymes) by which a particular substance is changed by an organism. Further information on metabolism may be obtained from The Pharmacological Basis of Therapeutics, 9th Edition, McGraw-Hill (1996). Metabolites of the (modified) non-natural amino acid polypeptide disclosed herein can be identified either by administration of (modified) non-natural amino acid polypeptide to a host and analysis of tissue samples from the host, or by incubation of (modified) non-natural amino acid polypeptide with hepatic cells in vitro and analysis of the resulting compounds.

The term "modified," as used herein refers to the presence of a post-translational modification on a polypeptide. The form "(modified)" term means that the polypeptides being discussed are optionally modified, that is, the polypeptides under discussion can be modified or unmodified.

As used herein, the term "modulated serum half-life" means the positive or negative change in circulating half-life of a modified polypeptide relative to its non-modified form. Serum half-life is measured by taking blood samples at various time points after administration of the polypeptide, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of therapeutically effective amount of a modified polypeptide, relative to its non-modified form. Therapeutic half-life is measured by measuring pharmacokinetic and/or pharmacodynamic properties of the polypeptide at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida* etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix,* etc.) phylogenetic domain.

A "non-natural amino acid" refers to an amino acid that is not one of the 20 common amino acids or pyrrolysine or selenocysteine; other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

The term "nucleic acid" refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

As used herein, the term "polyalkylene glycol" refers to polyethylene glycol, polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide bonds.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. A pro-drug includes a pharmacologically inactive, or reduced-activity, derivative of an active drug. Prodrugs may be designed to modulate the amount of a drug or biologically active molecule that reaches a desired site of action through the manipulation of the properties of a drug, such as physiochemical, biopharmaceutical, or pharmacokinetic properties. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug.

In prophylactic applications, compositions containing the (modified) non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc.

By way of example only, blocking/protecting groups may be selected from:

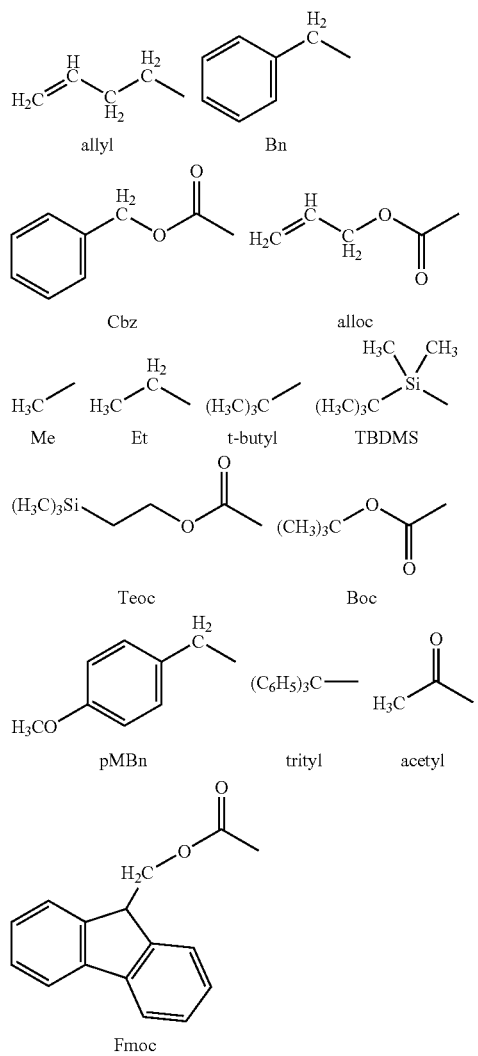

Other protecting groups are described in Greene and Wuts, Protective Groups in Organic Synthesis, 3rd Ed., John Wiley & Sons, New York, N.Y., 1999, which is incorporated herein by reference in its entirety.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. A wide variety of reducing agents are suitable for use in the methods and compositions described herein.

"Refolding," as used herein describes any process, reaction or method which transforms disulfide bond containing polypeptides from an improperly folded or unfolded state to a native or properly folded conformation with respect to disulfide bonds.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or PNA, other nucleic acid mimcs, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

The term "subject" as used herein, refers to an animal, in some embodiments a mammal, and in other embodiment a human, who is the object of treatment, observation or experiment.

The term "substantially purified" refers to a polypeptide that may be substantially or essentially free of components that normally accompany or interact with the protein as found in its naturally occurring environment, i.e. a native cell, or host cell in the case of recombinantly produced polypeptide. A polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" polypeptide as produced by the methods described herein may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

The term "substituents" includes but is not limited to "non-interfering substituents." "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—(C6-$C_{10}$ aryl), —$(CH_2)_m$—O—$(CH_2)_m$—O—($C_1$-$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R group in the preceding list is independently selected from the group consisting of H, alkyl or substituted alkyl, aryl or substituted aryl, or alkaryl. Where substituent groups are specified by their conventional chemical formulas, written from left to right, they equally encompass the chemically identical substituents that would result from writing the structure from right to left, for example, —$CH_2O$— is equivalent to —$OCH_2$—.

Substituents for alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR, =O, =NR, =N—OR, —$NR_2$, —SR, -halogen, —$SiR_3$, —OC(O)R, —C(O)R, —$CO_2$R, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2$R, —CN and —$NO_2$ in a number ranging from zero to (2m'+1), where m' is the total number of carbon atoms in such a radical. Each R group in the preceding list is independently selected from the group consisting of hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. When two R groups are attached to the same nitrogen atom, they can be combined with the nitrogen atom to form a 5-, 6-, or 7-membered ring. For example, —$NR_2$ is meant to include, but not be limited to, 1-pyrrolidinyl and 4-morpholinyl. From the above discussion of substituents, one of ordinary skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

Similar to the substituents described for the alkyl radical, substituents for aryl and heteroaryl groups are varied and are selected from, but are not limited to —OR, =O, =NR, =N—OR, —$NR_2$, —SR, -halogen, —$SiR_3$, —OC(O)R, —C(O)R, —$CO_2$R, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2$R, —CN, —$NO_2$, —R, —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where each R group in the preceding list is independently selected from hydrogen, alkyl, heteroalkyl, aryl and heteroaryl.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

As used herein, the term "water soluble polymer" refers to any polymer that is soluble in aqueous solvents. Linkage of water soluble polymers to a polypeptide can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include but are not limited to polyethylene glycol and serum albumin. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

Unless otherwise indicated, conventional methods of mass spectroscopy, NMR, HPLC, protein chemistry, biochemistry, recombinant DNA techniques and pharmacology, within the skill of the art are employed.

Compounds (including, but not limited to non-natural amino acids, (modified) non-natural amino acid polypeptides and reagents for producing either of the aforementioned compounds) presented herein include isotopically-labelled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

Some of the compounds herein (including, but not limited to non-natural amino acids, (modified) non-natural amino acid polypeptides and reagents for producing either of the aforementioned compounds) have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein (including, but not limited to non-natural amino acids, (modified) non-natural amino acid polypeptides and reagents for producing either of the aforementioned compounds) are used in the form of pro-drugs. In additional or further embodiments, the compounds described herein (including, but not limited to non-natural amino acids, (modified) non-natural amino acid polypeptides and reagents for producing either of the aforementioned compounds) are metabolized upon administration to an organism in need to produce a metabolite that is then used to produce a desired effect, including a desired therapeutic effect. In a further or additional embodiments are active metabolites of non-natural amino acids and (modified) non-natural amino acid polypeptides.

The methods and formulations described herein include the use of N-oxides, crystalline forms (also known as polymorphs), or pharmaceutically acceptable salts of non-natural amino acids and (modified) non-natural amino acid polypeptides. In some situations, non-natural amino acids and (modified) non-natural amino acid polypeptides may exist as tautomers. All tautomers are included within the scope of the non-natural amino acids and (modified) non-natural amino acid polypeptides presented herein. In addition, the non-natural amino acids and (modified) non-natural amino acid polypeptides described herein can exist in unsolvated as well as solvated forms with pharmaceutically acceptable solvents such as water, ethanol, and the like. The solvated forms of the non-natural amino acids and (modified) non-natural amino acid polypeptides presented herein are also considered to be disclosed herein.

Those of ordinary skill in the art will recognize that some of the compounds herein (including, but not limited to non-natural amino acids, (modified) non-natural amino acid polypeptides and reagents for producing either of the aforementioned compounds) can exist in several tautomeric forms. All such tautomeric forms are considered as part of the compositions described herein. Also, for example all enol-keto forms of any compounds (including, but not limited to non-natural amino acids, (modified) non-natural amino acid polypeptides and reagents for producing either of the aforementioned compounds) herein are considered as part of the compositions described herein.

Some of the compounds herein (including, but not limited to non-natural amino acids, (modified) non-natural amino acid polypeptides and reagents for producing either of the aforementioned compounds) are acidic and may form a salt with a pharmaceutically acceptable cation. Some of the compounds herein (including, but not limited to non-natural amino acids, (modified) non-natural amino acid polypeptides and reagents for producing either of the aforementioned compounds) can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

All publications and patents mentioned herein are incorporated herein by reference for the purpose of describing and disclosing, for example, the constructs and methodologies that are described in the publications, which might be used in connection with the presently described inventions. As one example, the following patent applications are disclosed in their entirety: 60/638,418; 60/696,210; 60/638,527; 60/696,302; 60/639,195; 60/696,068; 60/755,338; 60/755,711; 60/755,018; 60/743,041; 60/743,040; 60/734,589; Ser. Nos. 11/313,956; 11/313,306; and 11/313,305. The publications discussed herein are provided solely for their disclosure prior to the filing date of the present application. Nothing herein is to be construed as an admission that the inventors described herein are not entitled to antedate such disclosure by virtue of prior invention or for any other reason.

BRIEF DESCRIPTION OF THE FIGURES

A better understanding of the features and advantages of the present methods and compositions may be obtained by reference to the following detailed description that sets forth illustrative embodiments, in which the principles of our methods, compositions, devices and apparatuses are utilized, and the accompanying drawings of which.

DETAILED DESCRIPTION OF THE INVENTION

I. Introduction

Figure 1:
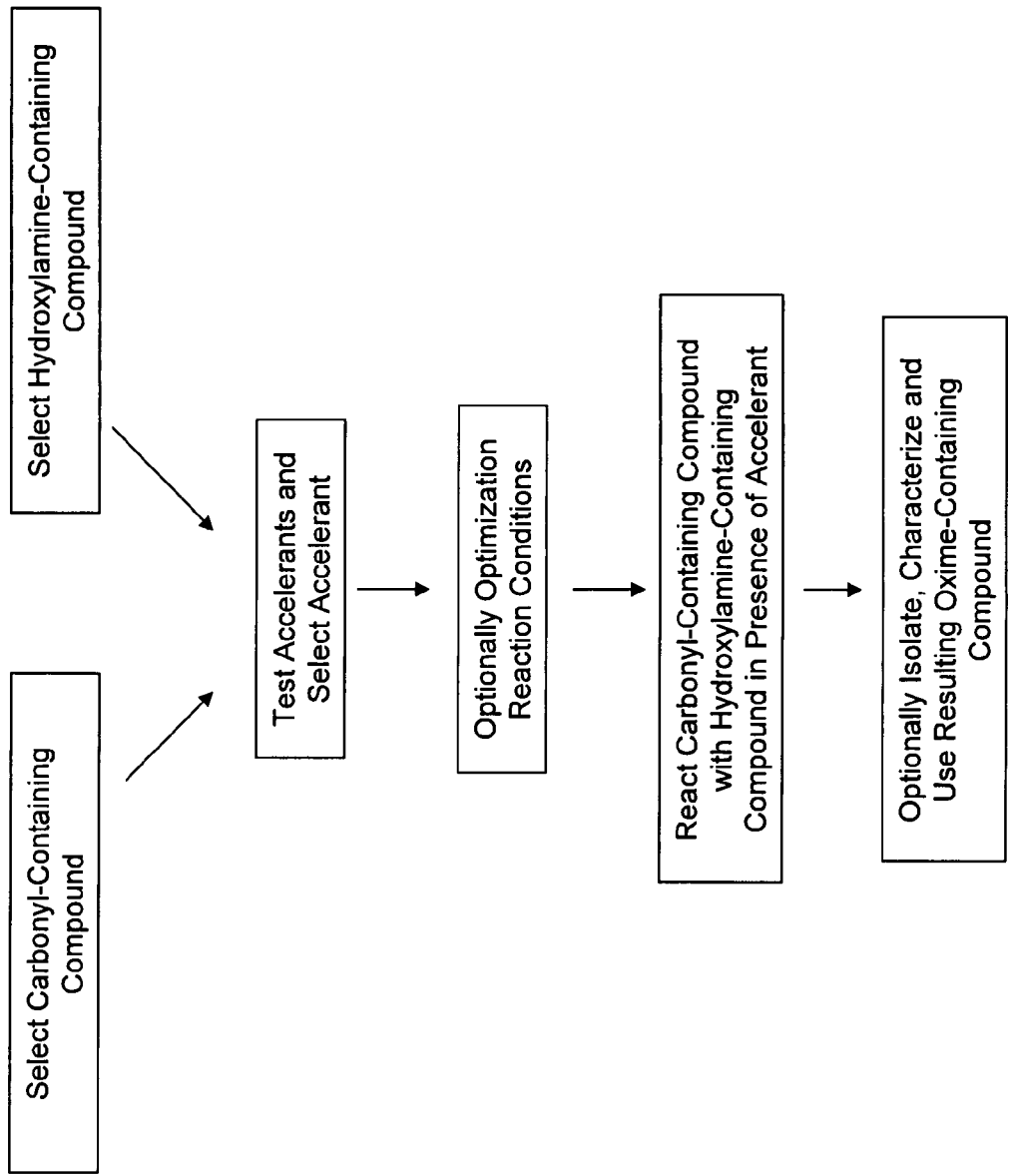
FIG. 1 presents a schematic representation of the relationship of certain aspects of the methods, compositions, strategies and techniques described herein.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-natural amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and Chin, J. W., et al. (2002) *J. Am. Chem. Soc.* 124:9026-27); keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027 (incorporated by reference in its entirety); J. W. Chin, & P. G. Schultz, (2002), *Chem Bio Chem* 3(11):1135-1137 (incorporated by reference in its entirety); J. W. Chin, et al., (2002), *PNAS United States of America* 99:11020-11024 (incorporated by reference in its entirety); and, L. Wang, & P. G. Schultz, (2002), *Chem. Comm.* 1:1-11 (incorporated by reference in its entirety). These studies have demonstrated that it is possible to selectively and routinely introduce chemical functional groups that are not found in proteins, that are chemically inert to all of the functional groups found in the 20 common, genetically-encoded amino acids (i.e., "natural" amino acids) and that may be used to react efficiently and selectively to form stable covalent linkages.

Chemical functional groups not found in the natural amino acids include carbonyl groups, such as ketones and aldehydes, and hydroxylamine groups. A hydroxylamine moiety reacts with a carbonyl group such as ketone and aldehyde to form a relatively stable oxime; this pairing (hydroxylamine with a carbonyl group) thus provides a means for further functionalizing non-natural amino acid polypeptides. One non-limiting example of such a pairing is shown below:

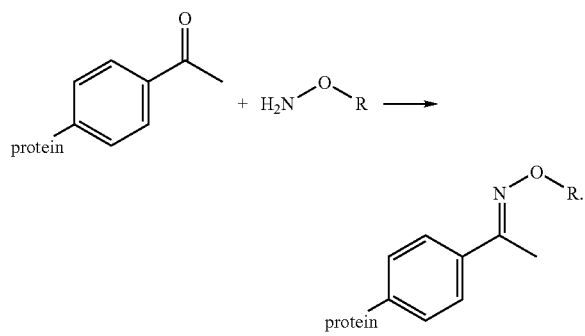

For example, when either a hydroxylamine moiety or a carbonyl group is incorporated into a non-natural amino acid polypeptide and reacted with a reagent that contains that other member of the pair, the non-natural amino acid polypeptide can be functionalized with the reagent via the formation of an oxime group. Though compatible for protein functionalization reactions, the standard oxime formation reaction may be made more efficient which would allow, for example, for the use of lower amounts of reactants and reduce the time to reaction completion. Therefore, the development of an accelerant is highly desirable.

II. Overview

FIG. 1 is one embodiment of the compositions, methods and techniques that are described herein. A carbonyl-containing compound is selected for reaction with a hydroxylamine-containing compound to form an oxime-containing compound. The carbonyl-containing compound includes non-natural amino acids, polypeptides, oligonucleotides, polymers (including by way of example only polyethylene glycol), reagents, linker groups, groups comprising further functionality, and combinations thereof; the present disclosure provides numerous examples of groups comprising further functionality. The hydroxylamine-containing compound includes non-natural amino acids, polypeptides, oligonucleotides, polymers (including by way of example only polyethylene glycol), reagents, linker groups, groups comprising further functionality, and combinations thereof; the present disclosure provides numerous examples of groups comprising further functionality. The oxime-containing compound includes non-natural amino acids, polypeptides, oligonucleotides, polymers (including by way of example only polyethylene glycol), reagents, linker groups, groups comprising further functionality, and combinations thereof; the present disclosure provides numerous examples of groups comprising further functionality. To the reaction mixture of the hydroxylamine-containing compound and the carbonyl-containing compound is added an accelerant, wherein the accelerant has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In a further embodiment, the accelerant has none of the aforementioned properties. Optionally, a variety of accelerants described herein are tested and an accelerant is selected based on its possession of at least one of the aforementioned properties. Optionally, the reaction characteristics (e.g., yield of oxime-containing compound) can be further optimized by at least one of the following: (a) varying the amount of accelerant, (b) varying the amount of carbonyl-containing compound, (c) varying the amount of hydroxylamine-containing compound, (d) varying the temperature of the reaction, (e) varying the pH of the reaction, and (f) varying the solvent in the reaction mixture. Optionally, additional accelerants are tested at an optimized reaction condition, or the selection and optimization steps are reversed, or the selection and optimization steps are repeated in an iterative fashion. The carbonyl-containing compound and the hydroxylamine-containing compound are reacted in the presence of the accelerant to form the oxime-containing compound. Optionally the progress of the reaction is monitored by a detection means, including by way of example only, chromatography. The oxime-containing compound resulting from the reaction of a carbonyl-containing compound and a hydroxylamine-containing compound in the presence of an accelerant can be optionally isolated, purified and characterized. The accelerant can be removed from the oxime-containing compound by a variety of methods, including by way of example only filtration, in vacuo techniques, chromatography, membrane-based bioseparation, electrophoresis, precipitation of the oxime-containing compound, distillation, or a combination thereof. Thus, in one embodiment described herein, the accelerants can be removed in vacuo from the oxime-containing material; however, in other embodiments described herein, the accelerants can be removed using any (or any combination) of the aforementioned methods. Isolation and purification signifies the removal of at least some non-oxime containing compound from the materials in the reaction mixture.

At one level, described herein are the tools (methods, compositions, techniques) for creating and using a polypeptide comprising at least one non-natural amino acid or modified non-natural amino acid with an oxime group formed in the presence of an accelerant (although such a reaction may be less efficient in the absence of an accelerant described herein). Such non-natural amino acids may contain further functionality, including but not limited to, a desired functionality.

Also described herein are non-natural amino acids that have or can be modified to contain an oxime moiety formed in the presence of an accelerant (although such a reaction may be less efficient in the absence of an accelerant described herein). Included with this aspect are methods for producing, purifying, characterizing and using such non-natural amino acids. In another aspect described herein are methods, strategies and techniques for incorporating at least one such non-natural amino acids into a polypeptide. Also included with this aspect are methods for producing, purifying, characterizing and using such polypeptides containing at least one such non-natural amino acids. Also included with this aspect are compositions of and methods for producing, purifying, characterizing and using polynucleotides (including DNA and RNA) that can be used to produce, at least in part, a polypeptide containing at least one non-natural amino acid that can react, in the presence of an accelerant (although such a reaction may be less efficient in the absence of an accelerant described herein) to form an oxime-containing non-natural amino acid polypeptide, including such a polypeptide that has been modified. Also included with this aspect are compositions of and methods for producing, purifying, characterizing and using cells that can express such polynucleotides that can be used to produce, at least in part, a polypeptide containing at least one non-natural amino acid.

Also included within the scope of the methods, compositions, strategies and techniques described herein are accelerants for reacting a reagent with a non-natural amino acid (containing a carbonyl or dicarbonyl group, hydroxylamine group, or protected forms thereof) that is part of a polypeptide so as to produce any of the aforementioned post-translational modifications. In general, the resulting post-translationally modified non-natural amino acid polypeptide will contain at least one oxime group; the resulting modified oxime-containing non-natural amino acid polypeptide may undergo subsequent modification reactions. Also included with this aspect are methods for selecting, producing, optimizing, purifying, characterizing and using such accelerants that can be used with any such post-translational modifications of such non-natural amino acid(s).

The non-natural amino acid containing polypeptide can contain at least one, at least two, at least three, at least four, at least five, at least six, at least seven, at least eight, at least nine, or ten or more non-natural amino acids containing an oxime group (or protected or masked forms thereof), wherein at least one oxime group was produced in the presence of the accelerants described herein, and further, such an oxime-containing non-natural amino acid polypeptide may optionally contain at least non-natural amino acid polypeptide containing one carbonyl or dicarbonyl group, hydroxylamine group, or protected forms thereof. The non-natural amino acids can be the same or different, for example, there can be 1, 2, 3, 4, 5, 6, 7, 8, 9, 10, 11, 12, 13, 14, 15, 16, 17, 18, 19, 20, or more different sites in the protein that comprise 1, 2, 3, 4, 5, 6, 7, 8, 9, 10, 11, 12, 13, 14, 15, 16, 17, 18, 19, 20, or more different non-natural amino acids. In certain embodiments, at least one, but fewer than all, of a particular amino acid present in a naturally occurring version of the protein is substituted with a non-natural amino acid.

The non-natural amino acid methods and compositions described herein provides conjugates of substances having a wide variety of functional groups (provided that at least one conjugate is chemically linked to a non-natural amino acid via an oxime group formed in the presence of the accelerants described herein), substituents or moieties, with other substances including but not limited to a desired functionality.

In another aspect of the compositions, methods, techniques and strategies described herein are methods for studying or using any of the aforementioned (modified) non-natural amino acid polypeptides. Included within this aspect, by way of example only, are therapeutic, diagnostic, assay-based, industrial, cosmetic, plant biology, environmental, energy-production, and/or military uses which would benefit from a polypeptide comprising a (modified) non-natural amino acid polypeptide or protein.

III. Post-Translational Modifications of Non-Natural Amino Acid Components of a Polypeptide in the Presence of at Least One Accelerant Methods, compositions, techniques and strategies have been developed to site-specifically incorporate non-natural amino acids during the in vivo translation of proteins. By incorporating a non-natural amino acid with a sidechain chemistry that is orthogonal to those of the naturally-occurring amino acids, this technology makes possible the site-specific derivatization of recombinant proteins. As a result, a major advantage of the methods, compositions, techniques and strategies described herein is that derivatized proteins can now be prepared as defined homogeneous products. However, the methods, compositions, reaction mixtures, techniques and strategies described herein involving an accelerant are not limited to non-natural amino acid polypeptides formed by in vivo protein translation techniques, but includes non-natural amino acid polypeptides formed by any technique, including by way of example only expressed protein ligation, chemical synthesis, ribozyme-based techniques (see, e.g., section herein entitled "Expression in Alternate Systems"). For convenience, the phrase "post-translational modification," when directed to the use of an accelerant to form an oxime bond on a non-natural amino acid polypeptide, includes non-natural amino acid polypeptides formed by any technique, including any in vivo and in vitro techniques, such as those described herein and known to those of ordinary skill in the art.

The ability to incorporate non-natural amino acids into recombinant proteins broadly expands the chemistries which may be implemented for derivatization. More specifically, protein derivatization to form an oxime bond on a non-natural amino acid portion of a polypeptide offers several advantages. First, the naturally occurring amino acids generally do not form oxime bonds and thus reagents designed to form oxime bonds will react site-specifically with the non-natural amino acid component of the polypeptide (assuming of course that the non-natural amino acid and the corresponding reagent have been designed to form an oxime bond), thus the ability to site-selectively derivatize proteins provides a single homogeneous product as opposed to the mixtures of derivatized proteins produced using prior art technology. Second, oxime adducts are stable under biological conditions, suggesting that proteins derivatized by oxime exchange are valid candidates for therapeutic applications. Third, the stability of the resulting oxime bond can be manipulated based on the identity (i.e., the functional groups and/or structure) of the non-natural amino acid to which the oxime bond has been formed. Thus, in some embodiments, the oxime bond to the non-natural amino acid polypeptide has a decomposition half life less than one hour, in other embodiments less than 1 day, in other embodiments less than 2 days, in other embodiments less than 1 week and in other embodiments more than 1 week. In yet other embodiments, the resulting oxime is stable for at least two weeks under mildly acidic conditions, in other embodiments the resulting oxime is stable for at least 5 days under mildly acidic conditions. In other embodiments, the non-natural amino acid polypeptide is stable for at least 1 day in a pH between about 2 and 8; in other embodiments, from a pH between about 2 to 6; in other embodiment, in a pH between about 2 to 4. In other embodiments, using the strategies, methods, compositions and techniques described herein, one of ordinary skill in the art will be able to synthesize an oxime bond to a non-natural amino acid polypeptide with a decomposition half-life tuned to the needs of that skilled artisan (e.g., for a therapeutic use such as sustained release, or a diagnostic use, or an industrial use or a military use).

The formation of an oxime-containing non-natural amino acid or non-natural amino acid polypeptide from the reaction of (a) a carbonyl-containing non-natural amino acid or carbonyl-containing non-natural amino acid polypeptide and a hydroxylamine-containing reagent, or (b) a hydroxylamine-containing non-natural amino acid or hydroxylamine-containing non-natural amino acid polypeptide and a carbonyl-containing reagent, can be enhanced by addition of an accelerant to the reaction mixture. An accelerant is a compound that has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

The use of an accelerant includes the use of a single accelerant or multiple accelerants. In addition, the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the accelerant includes compounds that can be substantially removed in vacuo from the resulting oxime-containing compound. Further, the accelerant includes compounds containing a diamine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

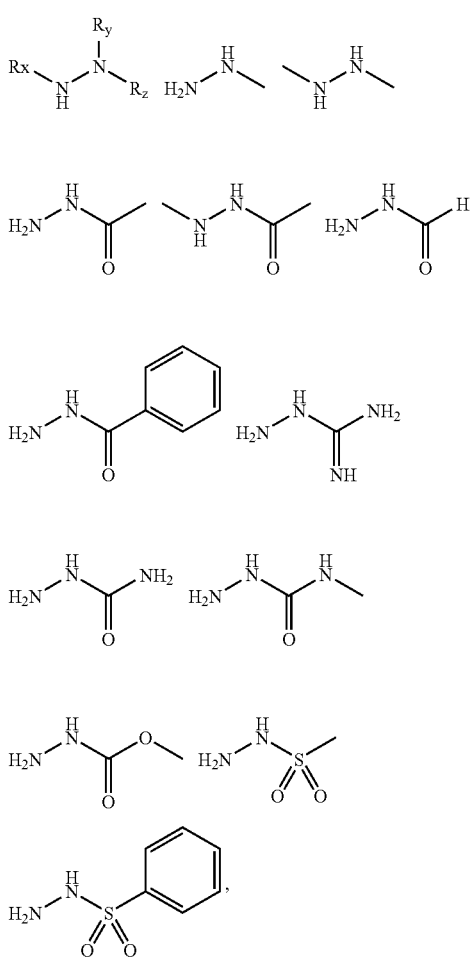

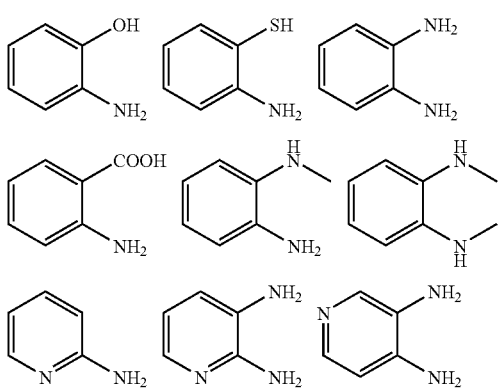

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

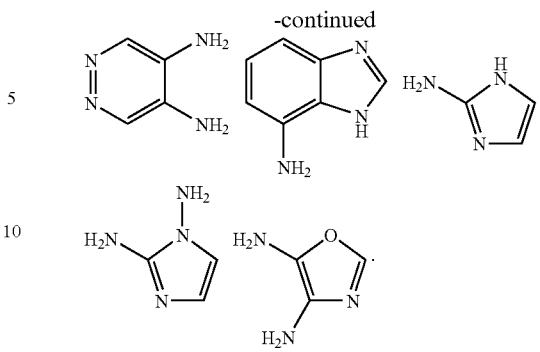

In a further embodiment, the accelerant is an oxoamine derivative. In a further embodiment, the oxoamine derivative is selected from the group:

Oxoamine Derivatives:

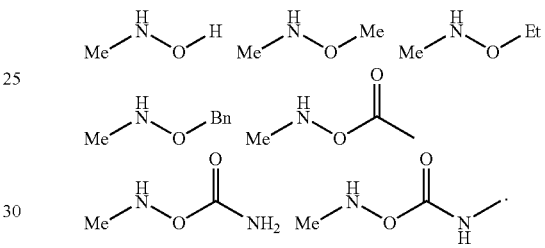

Figure 9:
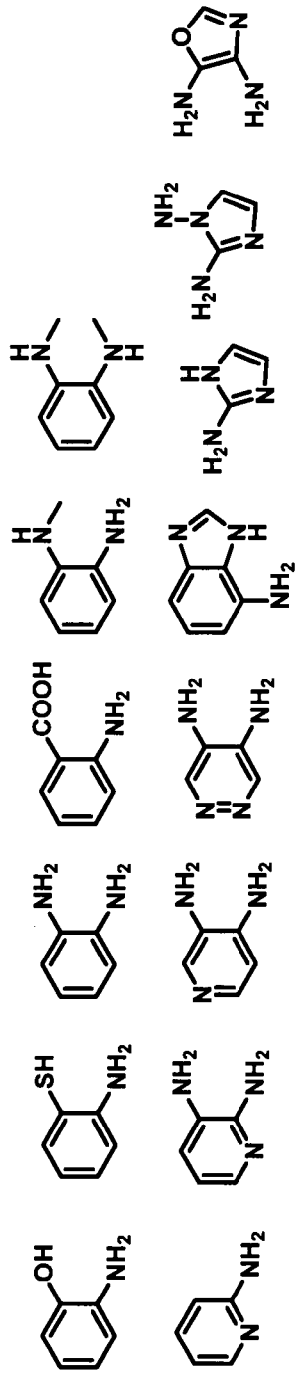
FIG. 9 presents non-limiting examples of accelerants that can be used in the methods, reactions and syntheses described herein.
Figure 9:
Figure 9:
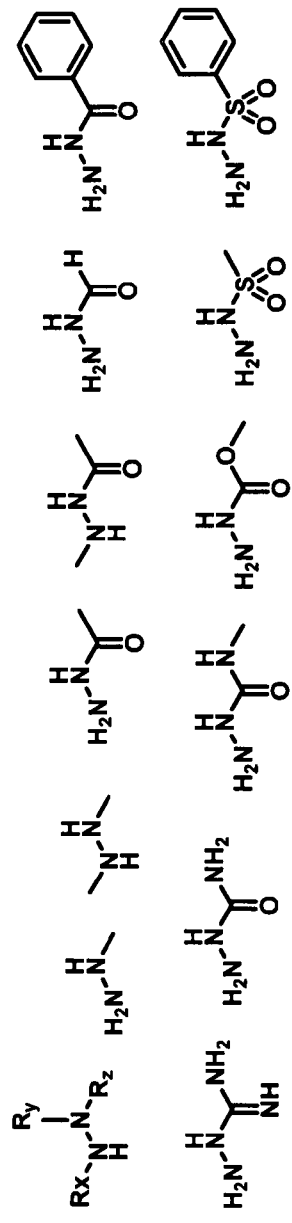
Figure 10:
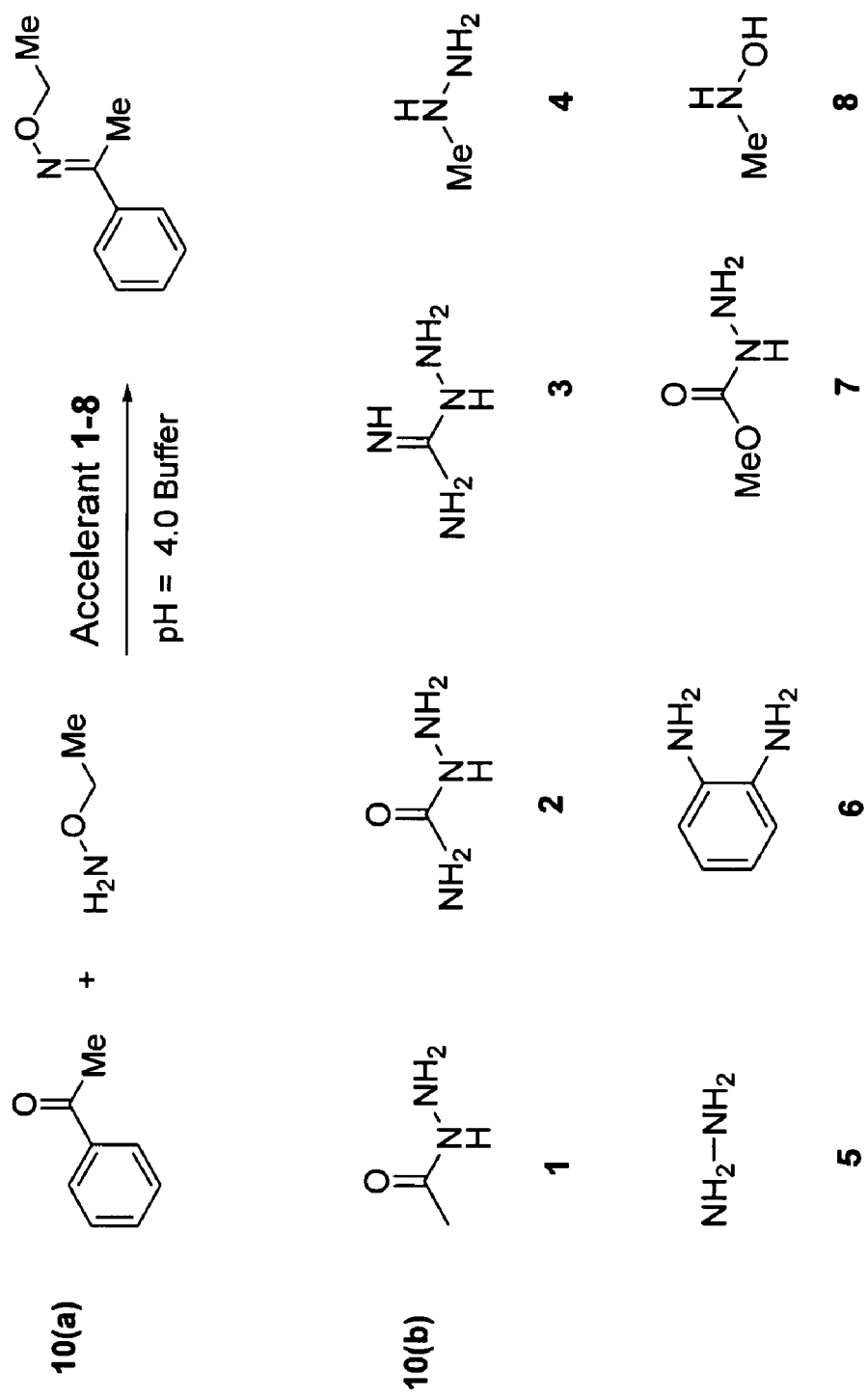
FIG. 10a presents a non-limiting reaction of a model ketone with a model hydroxylamine in the presence of an accelerant to form a model oxime.
FIG. 10b presents non-limiting examples of accelerants that can be used in the methods, reactions and syntheses described herein.

Further, the accelerant include compounds selected from the group consisting of:

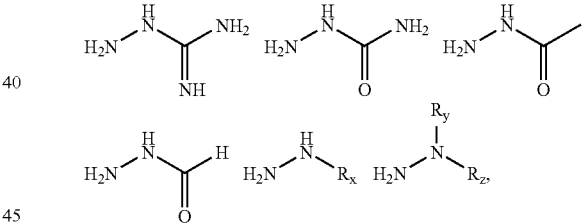

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10; between about 2.0 and 9.0; between about 2.0 and 8.0; between about 3.0 and 7.0; between about 4.0 and 6.0; between about 3.0 and 10.0; between about 4.0 and 10.0; between about 3.0 and 9.0; between about 3.0 and 8.0;

between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0.

The non-natural amino acid polypeptides described above are useful for, including but not limited to, novel therapeutics, diagnostics, catalytic enzymes, industrial enzymes, binding proteins (including but not limited to, antibodies and antibody fragments), and including but not limited to, the study of protein structure and function. See, e.g., Dougherty, (2000) *Unnatural Amino Acids as Probes of Protein Structure and Function, Current Opinion in Chemical Biology*, 4:645-652. Other uses for the non-natural amino acid polypeptides described above include, by way of example only, assay-based, cosmetic, plant biology, environmental, energy-production, and/or military uses. However, the non-natural amino acid polypeptides described above can undergo further modifications so as to incorporate new or modified functionalities, including manipulating therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications.

The methods, compositions, strategies and techniques described herein are not limited to a particular type, class or family of polypeptides or proteins. Indeed, virtually any polypeptides may include at least one non-natural amino acids described herein. By way of example only, the polypeptide can be homologous to a therapeutic protein selected from the group consisting of: alpha-1 antitrypsin, angiostatin, antihemolytic factor, antibody, antibody fragments, apolipoprotein, apoprotein, atrial natriuretic factor, atrial natriuretic polypeptide, atrial peptide, C—X—C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, I309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutropbil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-1, IGF-II, interferon (IFN), IFN-alpha, IFN-beta, IFN-gamma, any inteferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, FLT, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. The non-natural amino acid polypeptide may also be homologous to any polypeptide member of the growth hormone supergene family.

Such modifications include the incorporation of further functionality onto the non-natural amino acid component of the polypeptide, including but not limited to, a desired functionality.

Thus, by way of example only, a non-natural amino acid polypeptide containing any one of the following amino acids may be further modified in the presence of the accelerants described herein using the methods and compositions described herein:

(a)

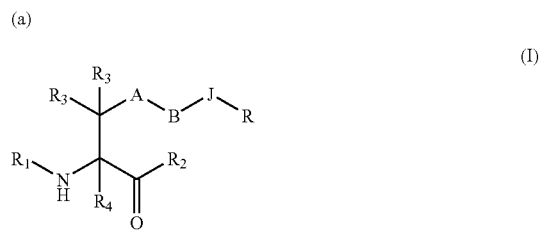

(I)

wherein:
  A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
  B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C (S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

J is

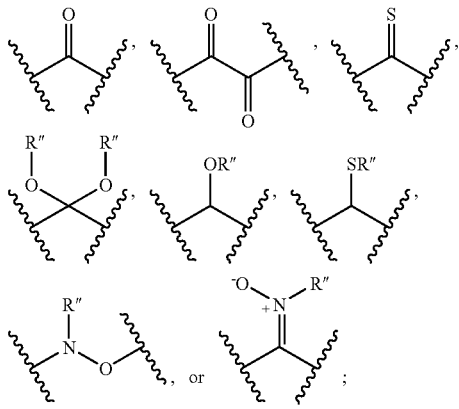

R is H, alkyl, substituted alkyl, cycloalkyl, or substituted cycloalkyl;
each R" is independently H, alkyl, substituted alkyl, or a protecting group, or when more than one R" group is present, two R" optionally form a heterocycloalkyl;
R$_1$ is optional, and when present, is H, an amino protecting group, resin; and
R$_2$ is optional, and when present, is OH, an ester protecting group, resin;
each of R$_3$ and R$_4$ is independently H, halogen, lower alkyl, or substituted lower alkyl, or R$_3$ and R$_4$ or two R$_3$ groups optionally form a cycloalkyl or a heterocycloalkyl;
or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;
or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

(b)

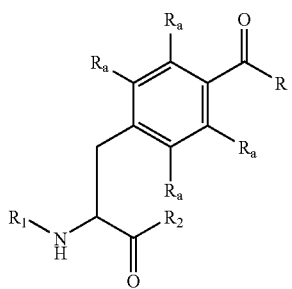

(III)

wherein:
R is alkyl, substituted alkyl, cycloalkyl, or substituted cycloalkyl;
R$_1$ is optional, and when present, is H, an amino protecting group, resin; and
R$_2$ is optional, and when present, is OH, an ester protecting group, resin; and
each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl, or substituted alkyl.

(c)

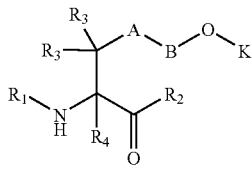

(XIV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;
K is —NR$_6$R$_7$ or —N=CR$_6$R$_7$;
R is H, alkyl, substituted alkyl, cycloalkyl, or substituted cycloalkyl;
R$_1$ is optional, and when present, is H, an amino protecting group, resin; and
R$_2$ is optional, and when present, is OH, an ester protecting group, resin;
each of R$_3$ and R$_4$ is independently H, halogen, lower alkyl, or substituted lower alkyl, or R$_3$ and R$_4$ or two R$_3$ groups optionally form a cycloalkyl or a heterocycloalkyl;
each of R$_6$ and R$_7$ is independently selected from the group consisting of H, alkyl, substituted alkyl, alkenyl, substituted alkenyl, alkoxy, substituted alkoxy, polyalkylene oxide, substituted polyalkylene oxide, aryl, substituted aryl, heteroaryl, substituted heteroaryl, alkaryl, substituted alkaryl, aralkyl, and substituted aralkyl, —C(O)R", —C(O)$_2$R", —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl; or $R_6$ or $R_7$ is L-X, where X is a selected from the group consisting of a desired functionality; and L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

(d)

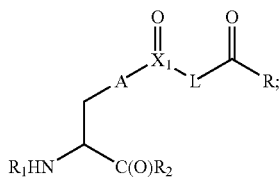

(XXX)

wherein;

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide;

$R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where each R' is independently H, alkyl, or substituted alkyl; or (e)

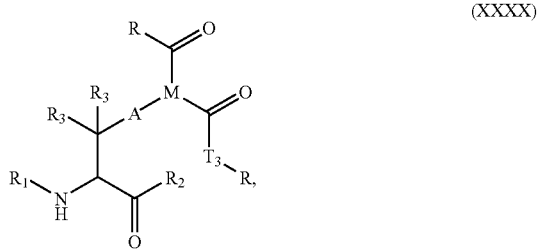

(XXXX)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is

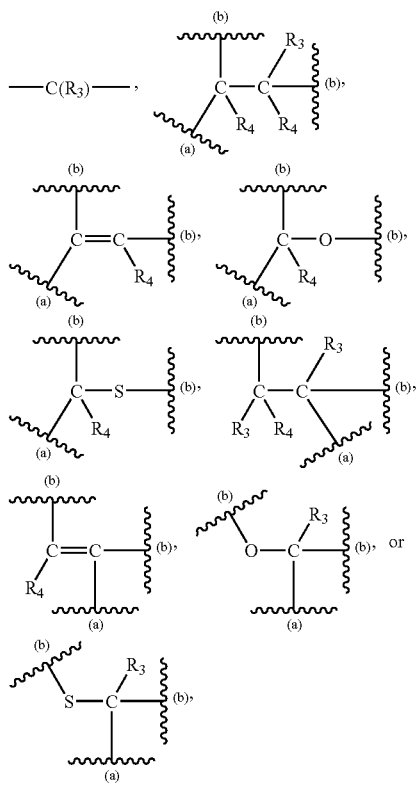

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

T$_3$ is a bond, C(R)(R), O, or S, and R is H, halogen, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide.

In one aspect of the methods and compositions described herein are compositions that include at least one protein with at least one, including but not limited to, at least two, at least three, at least four, at least five, at least six, at least seven, at least eight, at least nine, or at least ten or more non-natural amino acids that have been post-translationally modified. The post-translationally-modified non-natural amino acids can be the same or different, including but not limited to, there can be 1, 2, 3, 4, 5, 6, 7, 8, 9, 10, 11, 12, 13, 14, 15, 16, 17, 18, 19, 20, or more different sites in the protein that comprise 1, 2, 3, 4, 5, 6, 7, 8, 9, 10, 11, 12, 13, 14, 15, 16, 17, 18, 19, 20, or more different post-translationally-modified non-natural amino acids. In another aspect, a composition includes a protein with at least one, but fewer than all, of a particular amino acid present in the protein is substituted with the post-translationally-modified non-natural amino acid. For a given protein with more than one post-translationally-modified non-natural amino acids, the post-translationally-modified non-natural amino acids can be identical or different (including but not limited to, the protein can include two or more different types of post-translationally-modified non-natural amino acids, or can include two of the same post-translationally-modified non-natural amino acid). For a given protein with more than two post-translationally-modified non-natural amino acids, the post-translationally-modified non-natural amino acids can be the same, different or a combination of a multiple post-translationally-modified non-natural amino acid of the same kind with at least one different post-translationally-modified non-natural amino acid.

A. Methods for Post-Translationally Modifying Non-Natural Amino Acid Polypeptides in the Presence of at Least One Accelerant: Reactions of Carbonyl-Containing Non-Natural Amino Acids with Hydroxylamine-Containing Reagents The sidechains of the naturally occurring amino acids lack highly electrophilic sites. Therefore, the incorporation of an non-natural amino acid with an electrophile-containing sidechain, including, by way of example only, an amino acid containing a carbonyl or dicarbonyl group such as a ketone, makes possible the site-specific derivatization of this sidechain via nucleophilic attack of the carbonyl or dicarbonyl group. In the instance where the attacking nucleophile is a hydroxylamine, an oxime-derivatized protein will be generated. The methods for derivatizing and/or further modifying may be conducted with a polypeptide that has been purified prior to the derivatization step or after the derivatization step. Further, the derivatization step can occur under mildly acidic to slightly basic conditions, including by way of example, between a pH of about 2-8, or between a pH of about 4-8.

The formation of an oxime-containing non-natural amino acid or non-natural amino acid polypeptide from the reaction of a carbonyl-containing non-natural amino acid or carbonyl-containing non-natural amino acid polypeptide and a hydroxylamine-containing reagent can be enhanced by addition of an accelerant to the reaction mixture. An accelerant is a compound that has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

The use of an accelerant includes the use of a single accelerant or multiple accelerants. In addition, the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the accelerant includes compounds that can be substantially removed in vacuo from the resulting oxime-containing compound. Further, the accelerant includes compounds containing a diamine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

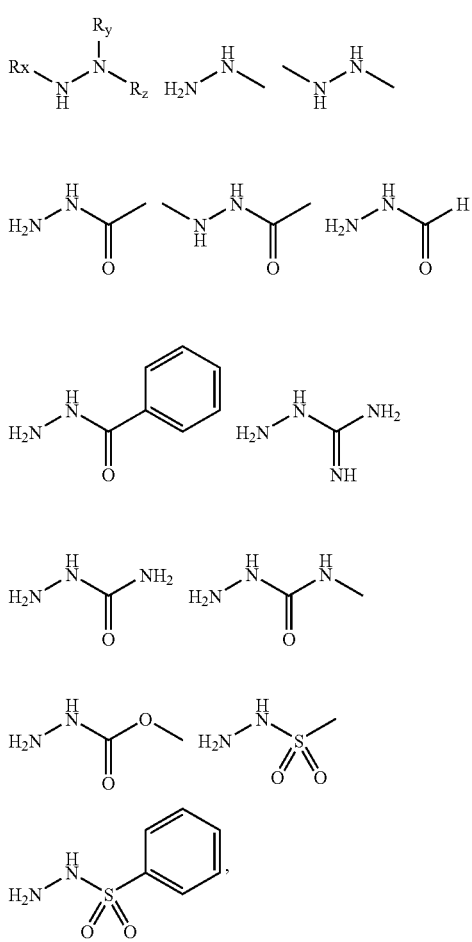

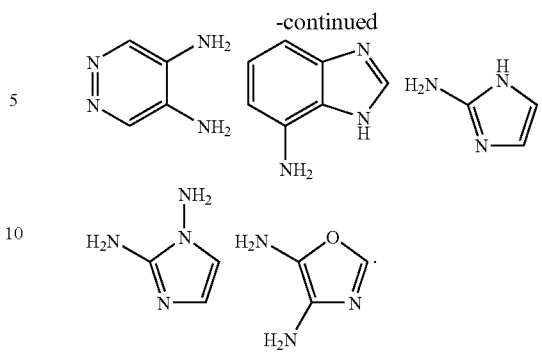

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

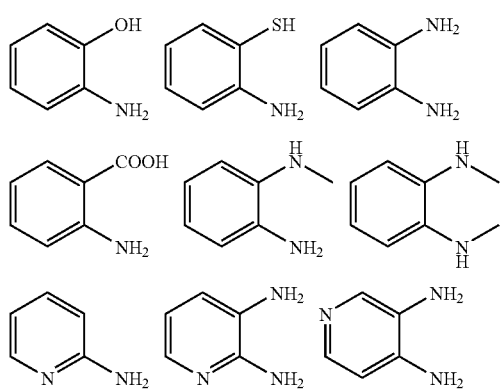

In a further embodiment, the accelerant is an oxoamine derivative. In a further embodiment, the oxoamine derivative is selected from the group:

Oxoamine Derivatives:

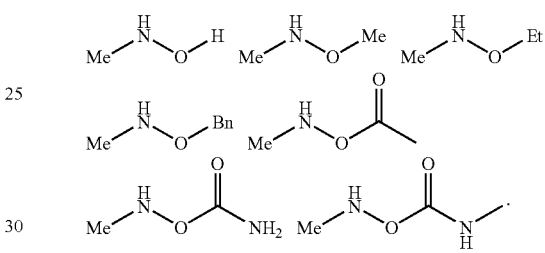

Further, the accelerant include compounds selected from the group consisting of:

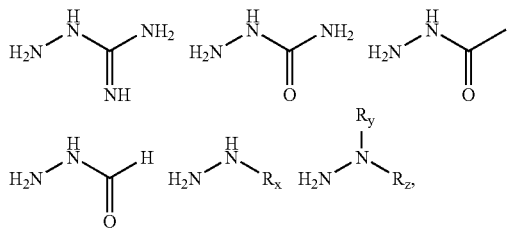

wherein $R_x$, $R^y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10; between about 2.0 and 9.0; between about 2.0 and 8.0; between about 3.0 and 7.0; between about 4.0 and 6.0; between about 3.0 and 10.0; between about 4.0 and 10.0; between about 3.0 and 9.0; between about 3.0 and 8.0;

between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0.

A protein-derivatizing method based upon the reaction of a carbonyl- or dicarbonyl-containing protein with a hydroxylamine-substituted molecule has distinct advantages. First, hydroxylamines undergo condensation with carbonyl- or dicarbonyl-containing compounds in a pH between about 2 and 8 (and in further embodiments in a pH between about 4 and 8) to generate oxime adducts. Under these conditions, the sidechains of the naturally occurring amino acids are unreactive. Second, such selective chemistry makes possible the site-specific derivatization of recombinant proteins: derivatized proteins can now be prepared as defined homogeneous products. Third, the mild conditions needed to effect the reaction of the hydroxylamines described herein with the carbonyl- or dicarbonyl-containing polypeptides described herein generally do not irreversibly destroy the tertiary structure of the polypeptide (excepting, of course, where the purpose of the reaction is to destroy such tertiary structure). Finally, although the hydroxylamine group amino appears to be metabolized by *E. coli*, the condensation of hydroxylamines with carbonyl- or dicarbonyl-containing molecules generates oxime adducts which are stable under biological conditions.

By way of example only, the following non-natural amino acids are the type of carbonyl- or dicarbonyl-containing amino acids that are reactive with the hydroxylamine-containing reagents described herein to form an oxime-containing non-natural amino acid or polypeptide in the presence of an accelerant described herein (although such a reaction may be less efficient in the absence of an accelerant described herein):

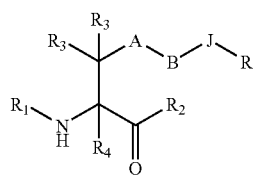
(I)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

J is

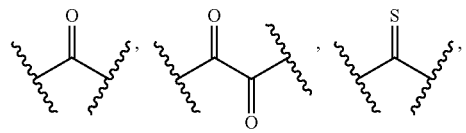

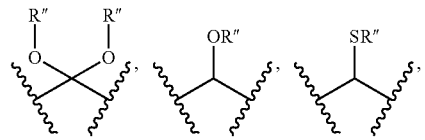

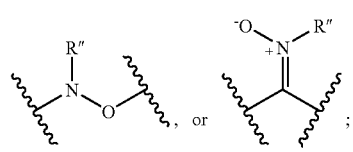

R is H, alkyl, substituted alkyl, cycloalkyl, or substituted cycloalkyl;
each R" is independently H, alkyl, substituted alkyl, or a protecting group, or when more than one R" group is present, two R" optionally form a heterocycloalkyl;
$R_1$ is optional, and when present, is H, an amino protecting group, resin; and
$R_2$ is optional, and when present, is OH, an ester protecting group, resin;
each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;
or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;
or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group.

By way of example only, for the aforementioned purposes, compounds of Formula (I) include compounds having the structure:

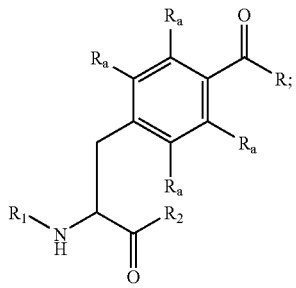

(III)

wherein:
- R is alkyl, substituted alkyl, cycloalkyl, or substituted cycloalkyl;
- $R_1$ is optional, and when present, is H, an amino protecting group, resin; and
- $R_2$ is optional, and when present, is OH, an ester protecting group, resin; and
- each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

By way of example only, for the aforementioned purposes, compounds of Formula (I) include compounds having the structure:

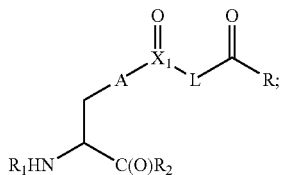

(XXX)

wherein;
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- R is alkyl, substituted alkyl, cycloalkyl, or substituted cycloalkyl;
- $R_1$ is optional, and when present, is H, an amino protecting group, resin, amino acid, polypeptide, or polynucleotide;
- $R_2$ is optional, and when present, is OH, an ester protecting group, resin, amino acid, polypeptide, or polynucleotide;
- $X_1$ is C, S, or S(O); and L is a bond, alkylene, substituted alkylene, N(R')(alkylene) or N(R') (substituted alkylene), where each R' is independently H, alkyl, or substituted alkyl.

By way of further example only, for the aforementioned purposes, compounds of Formula (I) include compounds having the structure of Formula (XXXX):

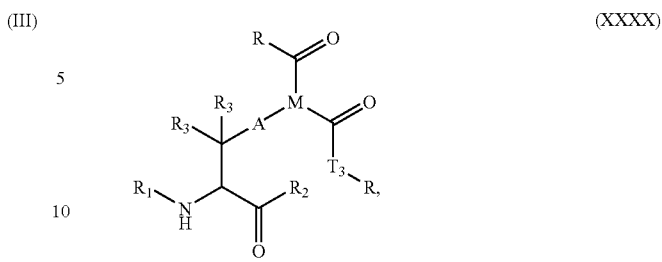

(XXXX)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is

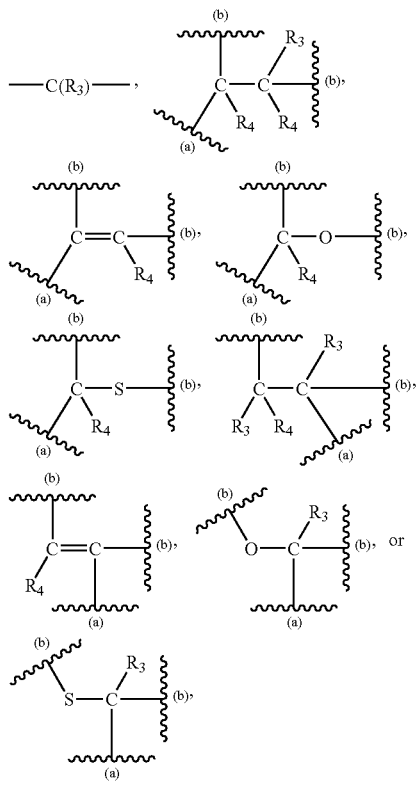

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is alkyl, substituted alkyl, cycloalkyl, or substituted cycloalkyl;

T3 is a bond, C(R)(R), O, or S, and R is H, halogen, alkyl substituted alkyl, cycloalkyl, or substituted cycloalkyl;

R₁ is optional, and when present, is H, an amino protecting group, resin, amino acid, polypeptide, or polynucleotide; and R₂ is optional, and when present, is OH, an ester protecting group, resin, amino acid, polypeptide, or polynucleotide.

The types of polypeptides that comprise such carbonyl- or dicarbonyl-containing non-natural amino acids is practically unlimited as long as the carbonyl- or dicarbonyl-containing non-natural amino acid is located on the polypeptide so that the hydroxylamine reagent can react with the carbonyl or dicarbonyl group and not create a resulting modified non-natural amino acid that destroys the tertiary structure of the polypeptide (excepting, of course, if such destruction is the purpose of the reaction).

By way of example only, the following hydroxylamine-containing reagents are the type of hydroxylamine-containing reagents that are reactive with the carbonyl- or dicarbonyl-containing non-natural amino acids described herein to form an oxime-containing non-natural amino acid in the presence of an accelerant described herein (although such a reaction may be less efficient in the absence of an accelerant described herein):

(XIX)

wherein:

each X is independently H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")₂, -(alkylene or substituted alkylene)-C(O)SR", -(alkylene or substituted alkylene)-S—S-(aryl or substituted aryl), —C(O)R", —C(O)₂R", or —C(O)N(R")₂, wherein each R" is independently hydrogen, alkyl, substituted alkyl, alkenyl, substituted alkenyl, alkoxy, substituted alkoxy, aryl substituted aryl, heteroaryl, alkaryl, substituted alkaryl, aralkyl, or substituted aralkyl;

or each X is independently selected from the group consisting of a desired functionality;

each L is independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N═, —C(R')═N—, —C(R')═N—N(R')—, —C(R')═N—N═, —C(R')₂—N═N—, and —C(R')₂—N(R')—N(R')—;

L₁ is optional, and when present, is —C(R')$_p$—NR'—C(O)O-(alkylene or substituted alkylene)-where p is 0, 1, or 2;

each R' is independently H, alkyl, or substituted alkyl;

W is —N(R₈)₂, where each R₈ is independently H or an amino protecting group; and n is 1 to 3; provided that L-L₁-W together provide at least one hydroxylamine group capable of reacting with a carbonyl (including a dicarbonyl) group on a non-natural amino acid or a (modified) non-natural amino acid polypeptide.

In an illustrative embodiment, a hydroxylamine-derivatized reagent is added to a buffered solution (pH 2-8) of a carbonyl-containing non-natural amino acid polypeptide and an accelerant. The resulting oxime-containing non-natural amino acid polypeptide is purified by HPLC, FPLC or size-exclusion chromatography.

In a further or alternative illustrative embodiment, the molar ratio of a compound of Formula (I) to a compound of Formula (XIX) is about 1:2; 1:1; 1.5:1; 1.5:2; 2:1; 1:1.5; 2:1.5; or 1.5 to 2.

In one embodiment, multiple linker chemistries can react site-specifically with a carbonyl- or dicarbonyl-substituted non-natural amino acid polypeptide to form an oxime bond in the presence of an accelerant described herein (although such a reaction may be less efficient in the absence of an accelerant described herein). In one embodiment, the linker methods described herein utilize linkers containing the hydroxylamine functionality on at least one linker termini (mono, bi- or multi-functional). The condensation of a hydroxylamine-derivatized linker with a keto-substituted protein generates a stable oxime bond. Bi- and/or multi-functional linkers (e.g., hydroxylamine with one, or more, other linking chemistries) allow the site-specific connection of different molecules (e.g., other proteins, polymers or small molecules) to the non-natural amino acid polypeptide, while mono-functional linkers (hydroxylamine-substituted on all termini) facilitate the site-specific dimer- or oligomerization of the non-natural amino acid polypeptide. By combining this linker strategy with the in vivo translation technology described herein, it becomes possible to specify the three-dimensional structures of chemically-elaborated proteins.

B. Methods for Post-Translationally Modifying Non-Natural Amino Acid Polypeptides in the Presence of at Least One Accelerant: Reactions of Hydroxylamine-Containing Non-Natural Amino Acids with Carbonyl-Containing Reagents The post-translational modification techniques and compositions described above may also be used with hydroxylamine-containing non-natural amino acids reacting with carbonyl- or dicarbonyl-containing reagents to produce modified oxime-containing non-natural amino acid polypeptides in the presence of an accelerant described herein (although such a reaction may be less efficient in the absence of an accelerant described herein).

The formation of an oxime-containing non-natural amino acid or non-natural amino acid polypeptide from the reaction of a hydroxylamine-containing non-natural amino acid or hydroxylamine-containing non-natural amino acid polypeptide and a carbonyl-containing reagent can be enhanced by addition of an accelerant to the reaction mixture. An accelerant is a compound that has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

The use of an accelerant includes the use of a single accelerant or multiple accelerants. In addition, the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the accelerant includes compounds that can be substantially removed in vacuo from the resulting oxime-containing compound. Further, the accelerant includes compounds containing a diamine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

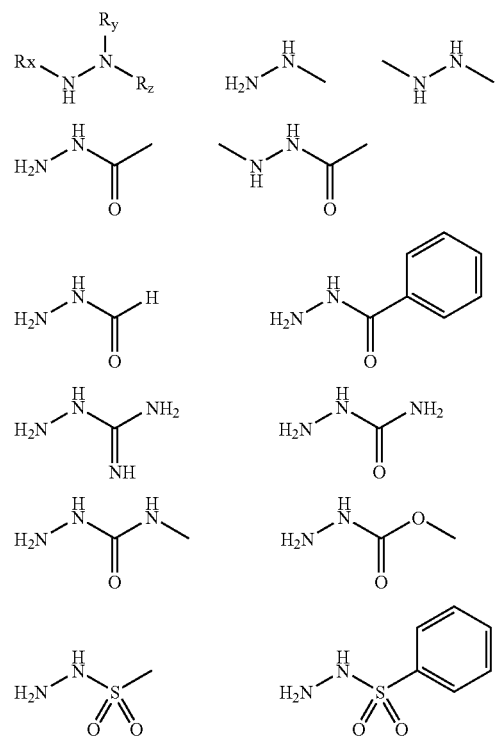

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

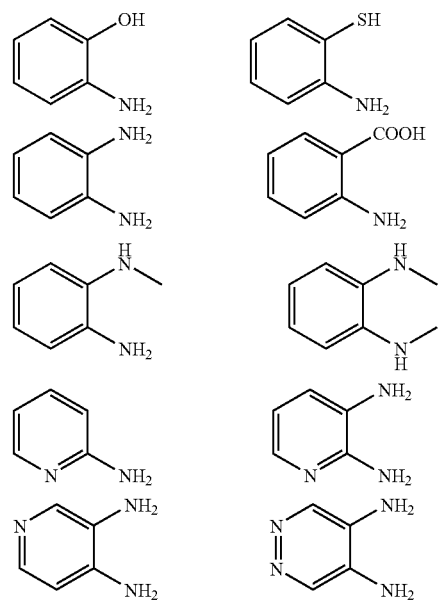

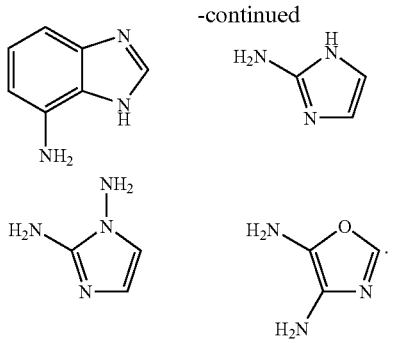

In a further embodiment, the accelerant is an oxoamine derivative. In a further embodiment, the oxoamine derivative is selected from the group:

Oxoamine Derivatives:

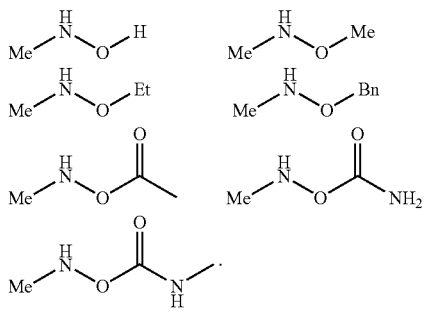

Further, the accelerant include compounds selected from the group consisting of:

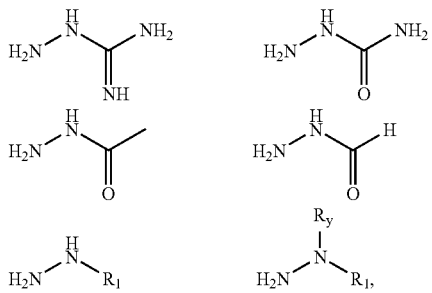

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects or embodiments, the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10; between about 2.0 and 9.0; between about 2.0 and 8.0; between about 3.0 and 7.0; between about 4.0 and 6.0; between about 3.0 and 10.0; between about 4.0 and 10.0; between about 3.0 and 9.0; between about 3.0 and 8.0; between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0.

A protein-derivatizing method based upon the reaction of a hydroxylamine-containing protein with a carbonyl- or dicarbonyl-substituted molecule has distinct advantages. First, hydroxylamines undergo condensation with carbonyl- or dicarbonyl-containing compounds in a pH between about 2 to 8 (and in further embodiments in a pH between about 4 to 8) to generate oxime adducts. Under these conditions, the sidechains of the naturally occurring amino acids are unreactive. Second, such selective chemistry makes possible the site-specific derivatization of recombinant proteins: derivatized proteins can now be prepared as defined homogeneous products. Third, the mild conditions needed to effect the reaction of the carbonyl- or dicarbonyl-containing reagents described herein with the hydroxylamine-containing polypeptides described herein generally do not irreversibly destroy the tertiary structure of the polypeptide (excepting, of course, where the purpose of the reaction is to destroy such tertiary structure). Finally, although the hydroxylamine group amino appears to be metabolized by *E. coli*, the condensation of carbonyl- or dicarbonyl-containing reagents with hydroxylamine-containing amino acids generates oxime adducts which are stable under biological conditions.

By way of example only, the following non-natural amino acids are the type of hydroxylamine-containing amino acids that are reactive with the carbonyl- or dicarbonyl-containing reagents described herein to form an oxime-containing non-natural amino acid or polypeptide in the presence of an accelerant described herein (although such a reaction may be less efficient in the absence of an accelerant described herein):

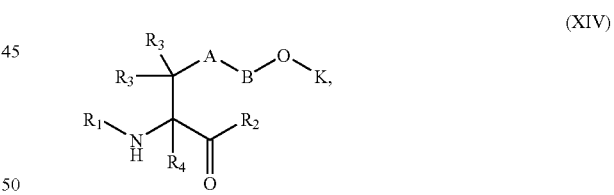

(XIV)

wherein:
  A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
  B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

K is —NH$_2$;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each of R$_3$ and R$_4$ is independently H, halogen, lower alkyl, or substituted lower alkyl, or R$_3$ and R$_4$ or two R$_3$ groups optionally form a cycloalkyl or a heterocycloalkyl.

The types of polypeptides that comprise such hydroxylamine-containing non-natural amino acids is practically unlimited as long as the hydroxylamine-containing non-natural amino acid is located on the polypeptide so that the carbonyl- or dicarbonyl-containing reagent can react with the hydroxylamine group and not create a resulting modified non-natural amino acid that destroys the tertiary structure of the polypeptide (excepting, of course, if such destruction is the purpose of the reaction).

By way of example only, the following carbonyl- or dicarbonyl-containing reagents are the type of carbonyl- or dicarbonyl-containing reagents that are reactive with the hydroxylamine-containing non-natural amino acids described herein to form an oxime-containing non-natural amino acid or polypeptide in the presence of an accelerant described herein (although such a reaction may be less efficient in the absence of an accelerant described herein):

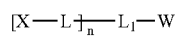  (XIX)

wherein:

each X is independently H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl;

or each X is independently selected from the group consisting of a desired functionality;

each L is independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—;

L$_1$ is optional, and when present, is —C(R')$_p$—NR'—C(O)O-(alkylene or substituted alkylene)—where p is 0, 1, or 2;

each R' is independently H, alkyl, or substituted alkyl;

W is -J-R, where

J is 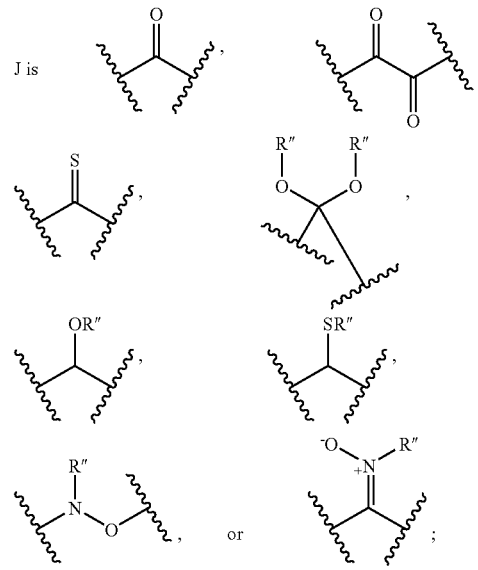

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl; and n is 1 to 3;

provided that L-L$_x$-W together provide at least one carbonyl group (including a dicarbonyl group) capable of reacting with an hydroxylamine group on a non-natural amino acid or a (modified) non-natural amino acid polypeptide.

In an illustrative embodiment, a carbonyl-derivatized reagent is added to a buffered solution (pH 2-8) of a hydroxylamine-containing non-natural amino acid polypeptide and an accelerant. The resulting oxime-containing non-natural amino acid polypeptide is purified by HPLC, FPLC or size-exclusion chromatography.

In a further or alternative illustrative embodiment, the molar ratio of a compound of Formula (XIV) to a compound of Formula (XIX) is about 1:2; 1:1; 1.5:1; 1.5:2; 2:1; 1:1.5; 2:1.5; or 1.5 to 2.

In one embodiment, multiple linker chemistries can react site-specifically with a hydroxylamine-substituted non-natural amino acid polypeptide. In one embodiment, the linker methods described herein utilize linkers containing the carbonyl or dicarbonyl functionality on at least one linker termini (mono, bi- or multi-functional). The condensation of a carbonyl- or dicarbonyl-derivatized linker with a hydroxylamine-substituted protein generates a stable oxime bond. Bi- and/or multi-functional linkers (e.g., carbonyl or dicarbonyl with one, or more, other linking chemistries) allow the site-specific connection of different molecules (e.g., other proteins, polymers or small molecules) to the non-natural amino acid polypeptide, while mono-functional linkers (carbonyl- or dicarbonyl-substituted on all termini) facilitate the site-specific dimer- or oligomerization of the non-natural amino acid polypeptide. By combining this linker strategy with the in vivo translation technology described herein, it becomes possible to specify the three-dimensional structures of chemically-elaborated proteins.

C. Example of Adding Functionality in the Presence of at Least One Accelerant: Macromolecular Polymers Coupled to Non-Natural Amino Acid Polypeptides Various modifications to the non-natural amino acid polypeptides described herein can be effected using the compositions, methods, techniques and strategies described herein. These modifications include the incorporation of further functionality onto the non-natural amino acid component of the polypeptide via an oxime bond formed in the presence of an accelerant described herein (although such a reaction may be less efficient in the absence of an accelerant described herein), including but not limited to, a desired functionality. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of ordinary skill in the art could make with the disclosures herein) to adding other functionalities, including but not limited to those listed above.

The formation of a macromolecular polymer coupled via an oxime bond to a non-natural amino acid polypeptide from (a) the reaction of a hydroxylamine-containing non-natural amino acid polypeptide and a carbonyl-containing reagent, or (b) the reaction of a carbonyl-containing non-natural amino acid polypeptide and a hydroxylamine-containing reagent, can be enhanced by addition of an accelerant to the reaction mixture. Such an accelerant is a compound that has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

The use of an accelerant includes the use of a single accelerant or multiple accelerants. In addition, the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the accelerant includes compounds that can be substantially removed in vacuo from the resulting oxime-containing compound. Further, the accelerant includes compounds containing a diamine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

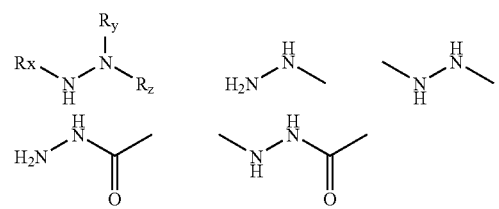

-continued

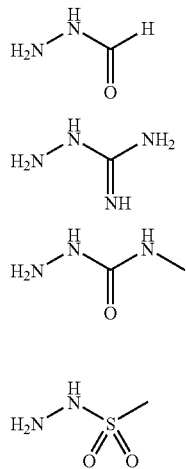
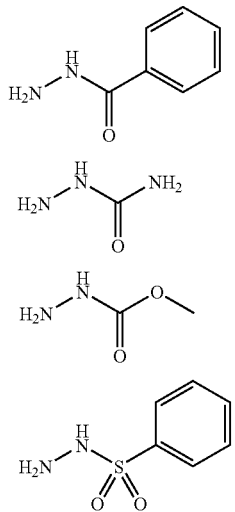

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

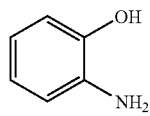
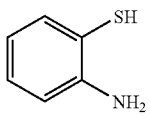
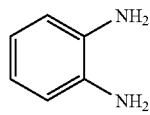
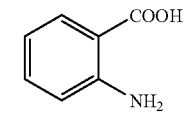
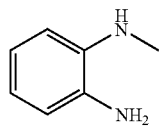
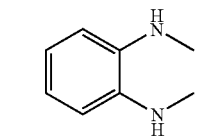
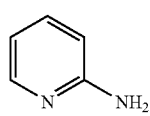
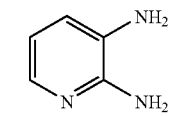
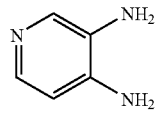
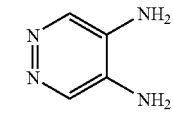
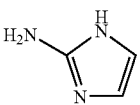

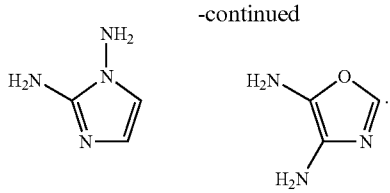

In a further embodiment, the accelerant is an oxoamine derivative. In a further embodiment, the oxoamine derivative is selected from the group:

Oxoamine Derivatives:

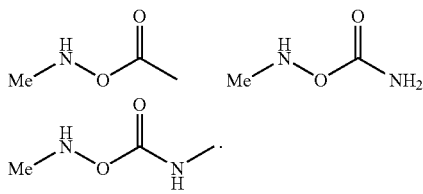

Further, the accelerant include compounds selected from the group consisting of:

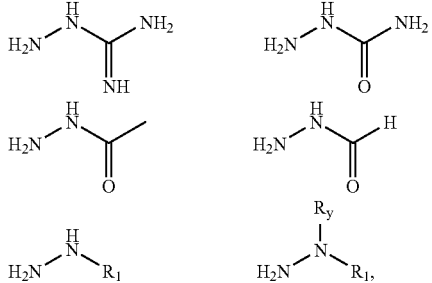

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10;

between about 2.0 and 9.0; between about 2.0 and 8.0; between about 3.0 and 7.0; between about 4.0 and 6.0; between about 3.0 and 10.0; between about 4.0 and 10.0; between about 3.0 and 9.0; between about 3.0 and 8.0; between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0.

A wide variety of macromolecular polymers and other molecules can be coupled to the non-natural amino acid polypeptides described herein to modulate biological properties of the non-natural amino acid polypeptide (or the corresponding natural amino acid polypeptide), and/or provide new biological properties to the non-natural amino acid polypeptide (or the corresponding natural amino acid polypeptide). These macromolecular polymers can be coupled to the non-natural amino acid polypeptide via an oxime bond on the non-natural amino acid.

Water soluble polymers can be coupled to the non-natural amino acid polypeptides described herein. The water soluble polymer may be coupled to the non-natural amino acid by an oxime bond. In some cases, the non-natural amino acid polypeptides described herein comprise one or more non-natural amino acid(s) linked to water soluble polymers and one or more naturally-occurring amino acids linked to water soluble polymers. Covalent attachment of hydrophilic polymers to a biologically active molecule represents one approach to increasing water solubility (such as in a physiological environment), bioavailability, increasing serum half-life, increasing therapeutic half-life, modulating immunogenicity, modulating biological activity, or extending the circulation time of the biologically active molecule, including proteins, peptides, and particularly hydrophobic molecules. Additional important features of such hydrophilic polymers include biocompatibility, lack of toxicity, and lack of immunogenicity. Preferably, for therapeutic use of the end-product preparation, the polymer will be pharmaceutically acceptable.

Examples of suitable hydrophilic polymers include: polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinylalcohols; copolymers thereof; terpolymers thereof; mixtures thereof; and derivatives of the foregoing. The water soluble polymer may be any structural form including but not limited to linear, forked or branched. In some embodiments, polymer backbones that are water-soluble, with from 2 to about 300 termini, are particularly useful. Multifunctional polymer derivatives include, but are not limited to, linear polymers having two termini, each terminus being bonded to a functional group which may be the same or different. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. Those of ordinary skill in the art will recognize that the foregoing list for substantially water soluble backbones is by no means exhaustive and is merely illustrative, and that all polymeric materials having the qualities described above are contemplated as being suitable for use in methods and compositions described herein.

As described above, one example of a hydrophilic polymer is poly(ethylene glycol), abbreviated PEG, which has been used extensively in pharmaceuticals, on artificial implants, and in other applications where biocompatibility, lack of toxicity, and lack of immunogenicity are of importance. The polymer:polyeptide embodiments described herein will use PEG as an example hydrophilic polymer with the understanding that other hydrophilic polymers may be similarly utilized in such embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects.

The term "PEG" is used broadly to encompass any polyethylene glycol molecule, without regard to size or to modification at an end of the PEG, and can be represented as linked to a non-natural amino acid polypeptide by the formula:

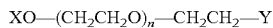

XO—(CH$_2$CH$_2$O)$_n$—CH$_2$CH$_2$—Y where n is 2 to 10,000 and X is H or a terminal modification, including but not limited to, a C$_{1-4}$ alkyl, a protecting group, or a terminal functional group. The term PEG includes, but is not limited to, poly(ethylene glycol) in any of its forms, including bifunctional PEG, multiarmed PEG, derivatized PEG, forked PEG, branched PEG (with each chain having a molecular weight of from about 1 kDa to about 100 kDa, from about 1 kDa to about 50 kDa, or from about 1 kDa to about 20 kDa), pendent PEG (i.e. PEG or related polymers having one or more functional groups pendent to the polymer backbone), or PEG with degradable linkages therein. In one embodiment, PEG in which n is from about 20 to about 2000 is suitable for use in the methods and compositions described herein. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In some cases, a PEG terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-natural amino acids to form an oxime group in the presence of an accelerant described herein (although such a reaction may be less efficient in the absence of an accelerant described herein); examples of the latter include but are not limited to, carbonyl or dicarbonyl and hydroxylamine groups.

It is noted that the other end of the PEG, which is shown in the above formula by Y, will attach either directly or indirectly to a polypeptide via a non-natural amino acid. When Y is a hydroxylamine group, then the hydroxylamine-containing PEG reagent can react with a carbonyl- or dicarbonyl-containing non-natural amino acid in a polypeptide to form a PEG group coupled to the polypeptide via an oxime bond in the presence of an accelerant described herein (although such a reaction may be less efficient in the absence of an accelerant described herein). When Y is a carbonyl or dicarbonyl group, then the carbonyl- or dicarbonyl-containing PEG reagent can react with a hydroxylamine-containing non-natural amino acid in a polypeptide to form a PEG group coupled to the polypeptide via an oxime bond in the presence of an accelerant described herein (although such a reaction may be less efficient in the absence of an accelerant described herein).

Heterobifunctional derivatives are also particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In some embodiments, a strong nucleophile (including but not limited to hydroxylamine) can be reacted with an carbonyl group, including a ketone group present in a non-natural amino acid to form an oxime in the presence of an accelerant described herein (although such a reaction may be less efficient in the absence of an accelerant described herein); the subsequent oxime group in some cases can be further reduced by treatment with an appropriate reducing agent. Alternatively, the strong nucleophile can be incorporated into the polypeptide via a non-natural amino acid and used to react preferentially with a carbonyl group, including a ketone group present in the water soluble polymer to form an oxime group in the presence of an accelerant described herein (although such a reaction may be less efficient in the absence of an accelerant described herein). Generally, at least one terminus of the PEG molecule is available for reaction with the non-natural amino acid.

The polymer backbone can be linear or branched. Branched polymer backbones are generally known in the art. Typically, a branched polymer has a central branch core moiety and a plurality of linear polymer chains linked to the central branch core. PEG is used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(—PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group, n is 100-1,000 (i.e., average molecular weight is between about 5 kDa to about 40 kDa), and Z is an activated terminal group linked to CH by a chain of atoms of defined length. Yet another branched form, the pendant PEG, has reactive groups, such as carboxyl, along the PEG backbone rather than at the end of PEG chains.

In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

The methods and compostions described herein may be used to produce substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated polypeptide preparations provided herein are those which are homogenous enough to display the advantages of a homogenous preparation, e.g., ease in clinical application in predictability of lot to lot pharmacokinetics.

As used herein, and when contemplating hydrophilic polymer:polypeptide/protein conjugates, the term "therapeutically effective amount" refers to an amount which provides benefit to a patient. The amount will vary from one individual to another and will depend upon a number of factors, including the overall physical condition of the patient and the underlying cause of the disease or condition. A therapeutically effective amount of the present compositions may be readily ascertained by one of ordinary skill in the art using publicly available materials and procedures. By way of example only, a therapeutically effective amount may be an amount which gives an increase in hematocrit for anemia patients; it may be an amount which decreases tumor size in cancer patients; it may be an amount which increases insulin levels in diabetic patients; or it may be an amount which decreases pain in patients suffering form chronic pain.

The number of water soluble polymers linked to a (modified) non-natural amino acid polypeptide (i.e., the extent of PEGylation or glycosylation) described herein can be adjusted to provide an altered (including but not limited to, increased or decreased) pharmacologic, pharmacokinetic or pharmacodynamic characteristic such as in vivo half-life. In some embodiments, the half-life of the polypeptide is increased at least about 10, 20, 30, 40, 50, 60, 70, 80, 90 percent, two fold, five-fold, 10-fold, 50-fold, or at least about 100-fold over an unmodified polypeptide.

In one embodiment, a polypeptide comprising a carbonyl- or dicarbonyl-containing non-natural amino acid is modified, in the presence of an accelerant, with a PEG derivative that contains a terminal hydroxylamine moiety that is linked directly to the PEG backbone, thus forming an oxime bond (although such a reaction may be less efficient in the absence of an accelerant described herein). In some embodiments, the hydroxylamine-terminal PEG derivative will have the structure:

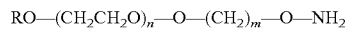

RO—(CH$_2$CH$_2$O)$_n$—O—(CH$_2$)$_m$—O—NH$_2$ where R is a simple alkyl (methyl, ethyl, propyl, etc.), m is 2-10 and n is 100-1,000 (i.e., average molecular weight is between about 5 kDa to about 40 kDa). The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In another embodiment, a polypeptide comprising a carbonyl- or dicarbonyl-containing amino acid is modified with a PEG derivative that contains a terminal hydroxylamine moiety that is coupled to the PEG backbone by means of an amide bond, thus forming an oxime bond (although such a reaction may be less efficient in the absence of an accelerant described herein) further coupled to the PEG backbone by means of an amide bond. In some embodiments, the hydroxylamine-terminal PEG derivatives have the structure:

$$RO-(CH_2CH_2O)_n-O-(CH_2)_2-NH-C(O)(CH_2)_m-O-NH_2$$

where R is a simple alkyl (methyl, ethyl, propyl, etc.), m is 2-10 and n is 100-1,000 (i.e., average molecular weight is between about 5 kDa to about 40 kDA).

In another embodiment, a polypeptide comprising a carbonyl- or dicarbonyl-containing amino acid is modified with a branched PEG derivative that contains a terminal hydroxylamine moiety thus forming an oxime bond (although such a reaction may be less efficient in the absence of an accelerant described herein), with each chain of the branched PEG having an average molecular weight ranging from about 10 kDa to about 40 kDa and, in other embodiments, from about 5 kDa to about 20 kDa. In some embodiments, the PEG derivatives containing a hydroxylamine group will have the structure:

$$[RO-(CH_2CH_2O)_n-O-(CH_2)_2-C(O)-NH-CH_2-CH_2]_2CH-X-(CH_2)_m-O-NH_2$$

where R is a simple alkyl (methyl, ethyl, propyl etc.), X is optionally NH, O, S, C(O) or not present, m is 2-10 and n is 100-1,000. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995). Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and more WO 93/15189, and for conjugation between activated polymers and enzymes including but not limited to Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)).

If necessary, the PEGylated non-natural amino acid polypeptides described herein obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta Ariz., PROTEIN PURIFICATION METHODS, A PRACTICAL APPROACH (Harris & Angal, Eds.) IRL Press 1989, 293-306). The purity of the non-natural amino acid polypeptide:PEG conjugate can be assessed by proteolytic degradation (including but not limited to, trypsin cleavage) followed by mass spectrometry analysis. Pepinsky R B, et.al., *J. Pharmcol. & Exp. Ther.* 297(3):1059-66 (2001).

D. Use of Linking Groups and Applications, Including Polypeptide Dimers and Multimers In addition to adding desired functionality directly to the non-natural amino acid polypeptide, the non-natural amino acid portion of the polypeptide may first be modified with a multifunctional (e.g., bi-, tri, tetra-) linker molecule that then subsequently is further modified. That is, at least one end of the multifunctional linker molecule reacts with at least one non-natural amino acid in a polypeptide and at least one other end of the multifunctional linker is available for further functionalization. If all ends of the multifunctional linker are identical, then (depending upon the stoichiometric conditions) homomultimers of the non-natural amino acid polypeptide may be formed. If the ends of the multifunctional linker have distinct chemical reactivities, then at least one end of the multifunctional linker group can react to as to be bound to the non-natural amino acid polypeptide and the other end can subsequently react with a different functionality, including by way of example only, a desired functionality.

The multifunctional linker group has the general structure:

(XIX)

wherein:
each X is independently $NH_2$, $-C(=O)R_9$, $-SR'$ or -J-R, where $R_9$ is H or OR', where J is

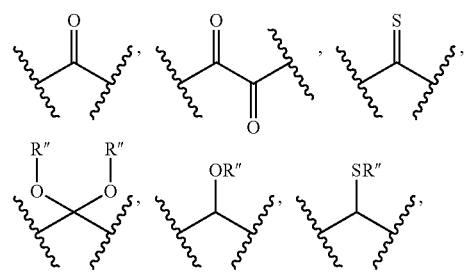

-continued

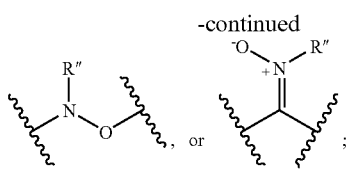

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl;

each R' is independently H, alkyl, or substituted alkyl;

each L is independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—;

L$_1$ is optional, and when present, is —C(R')$_p$—NR'—C(O)O-(alkylene or substituted alkylene)-where p is 0, 1, or 2;

W is NH$_2$, —C(=O)R$_9$, —SR' or -J-R; and n is 1 to 3 provided that X and L-L$_1$-W together independently each provide at least one of the following (a) a hydroxylamine group capable of reacting with a carbonyl (including a dicarbonyl) group on a non-natural amino acid or a (modified) non-natural amino acid polypeptide; (b) a carbonyl group (including a dicarbonyl group) capable of reacting with an hydroxylamine group on a non-natural amino acid or a (modified) non-natural amino acid polypeptide; or (c) a carbonyl group (including a dicarbonyl group) capable of undergoing an exchange reaction with an oxime group on a non-natural amino acid or a (modified) non-natural amino acid polypeptide.

In a further or alternative illustrative embodiment, the molar ratio of a compound of Formula (I) or Formula (XIV) to the multifunctional linker of Formula (XIX) is about 1:2; 1:1; 1.5:1; 1.5:2; 2:1; 1:1.5; 2:1.5; or 1.5 to 2.

A bifunctional homolinker in which the linker has two identical ends, i.e., hydroxylamine groups, can be used to form coupled polypeptides via the formation of oxime bonds, wherein the formation of such coupled polypeptides is performed in the presence of at least one accelerant (although the oxime bond may also occur at a slower reaction rate in the absence of the accelerant). The use of an accelerant described herein in the formation of polypeptide dimers and multimers is expected to provide significant benefit because that stoichiometric ratio of the linker to the first polypeptide, or the ratio of the linker-(first polypeptide) complex to the second polypeptide will be closer to stoichiometric in the presence of the accelerant than in the absence of the accelerant (or, further, as the molar ratio of accelerant increases, the closer the ratios of the aforementioned reactants will be to stoichiometric). The stoichiometric ratio (or molar ratio) is an important factor in the modification of polypeptides because of the expense of the reagents (including the polypeptide and the molecules for conjugation) and the difficulty in purification. Thus, the use of the accelerants provided herein can be used to reduce the cost and waste resulting from the modification of non-natural amino acid polypeptides, including the formation of polypeptide dimers or multimers, or the linking of any desired group or functionality to a polypeptide.

Such a linker may be used to form a homodimer of a carbonyl- or dicarbonyl-containing non-natural amino acid polypeptide to form two oxime bonds either or both of which are formed in the presence of at least one accelerant (although the oxime bond may also occur at a slower reaction rate in the absence of the accelerant). Alternatively, if one end of such a linker is protected, then such a partially protected linker can be used to bind the unprotected hydroxylamine end to a carbonyl- or dicarbonyl-containing non-natural amino acid polypeptide via an oxime bond, leaving the other protected end available for further linking reactions following deprotection. Alternatively, careful manipulation of the stoichiometry of the reagents may provide a similar result (a heterodimer), albeit a result in which the desired heterodimer will likely be contaminated with some homodimer.

Such a linker may also be used to form a homodimer of a hydroxylamine-containing non-natural amino acid polypeptide to form two oxime bonds either or both of which are formed in the presence of at least one accelerant (although the oxime bond may also occur at a slower reaction rate in the absence of the accelerant). Alternatively, if one end of such a linker is protected, then such a partially protected linker can be used to bind the unprotected carbonyl end to a hydroxylamine-containing non-natural amino acid polypeptide via an oxime bond, leaving the other protected end available for further linking reactions following deprotection. Alternatively, careful manipulation of the stoichiometry of the reagents may provide a similar result (a heterodimer), albeit a result in which the desired heterodimer will likely be contaminated with some homodimer.

A multifunctional heterolinkers in which each linker has more than one type of terminal reactive group, i.e., hydroxylamine, oxime and thioester groups, can be used to form coupled polypeptides via the formation of at least one oxime bond, wherein the formation of the oxime bond is performed in the presence of at least one accelerant. Such a linker may be used to form a heterodimer of a non-natural amino acid polypeptide using the accelerant-promoted oxime-based chemistry discussed throughout this specification.

The methods and compositions described herein also provide for polypeptide combinations, such as homodimers, heterodimers, homomultimers, or heteromultimers (i.e., trimers, tetramers, etc.). By way of example only, the following description focuses on the GH supergene family members, however, the methods, techniques and compositions described in this section can be applied to virtually any other polypeptide which can provide benefit in the form of dimers and multimers, including by way of example only: alpha-1 antitrypsin, angiostatin, antihemolytic factor, antibody, antibody fragments, apolipoprotein, apoprotein, atrial natriuretic factor, atrial natriuretic polypeptide, atrial peptide, C—X—C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any inteferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, FLT, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. The non-natural amino acid polypeptide may also be homologous to any polypeptide member of the growth hormone supergene family.

Thus, encompassed within the methods, techniques and compositions described herein are a GH supergene family member polypeptide containing one or more non-natural amino acids bound to another GH supergene family member or variant thereof or any other polypeptide that is a non-GH supergene family member or variant thereof, either directly to the polypeptide backbone or via a linker. Due to its increased molecular weight compared to monomers, the GH supergene family member dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member dimers described herein will modulate the dimerization of the GH supergene family member receptor. In other embodiments, the GH supergene family member dimers or multimers described herein will act as a GH supergene family member receptor antagonist, agonist, or modulator.

In some embodiments, the methods and compositions described herein provide multimers comprising one or more GH supergene family member formed by reactions with water soluble activated polymers that have the structure:

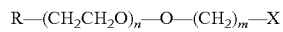

wherein n is from about 5 to 3,000, m is 2-10, X can be a hydroxylamine or carbonyl- or dicarbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

Using the chemistry detailed throughout this specification, one of ordinary skill in the art could design a linker in which at least one functional group can form an oxime group, in the presence of the accelerant disclosed herein, with a non-natural amino acid polypeptide; the other functional groups on the linker could utilize other known chemistry, including the nucleophile/electrophile based chemistry well known in the art of organic chemistry.

The formation of a polypeptide dimer or multimer linked together via at least one oxime group from (a) the reaction of a hydroxylamine-containing non-natural amino acid polypeptide and a carbonyl-containing reagent, or (b) the reaction of a carbonyl-containing non-natural amino acid polypeptide and a hydroxylamine-containing reagent, can be enhanced by addition of an accelerant to the reaction mixture. Such an accelerant is a compound that has at least one of the following properties: (a) increase the rate of reaction between a carbonyl-containing compound and a hydroxylamine-containing compound to form an oxime-containing compound, where the increase in rate is relative to the reaction in the absence of the accelerant; (b) lower the activation energy of the reaction between a carbonyl-containing compound and a hydroxylamine-containing compound to form an oxime-containing compound, where the decrease in activation energy is relative to the reaction in the absence of the accelerant; (c) increase the yield of an oxime-containing compound from the reaction of a carbonyl-containing compound with a hydroxylamine-containing compound, where the increase in yield is relative to the reaction in the absence of the accelerant; (d) lower the temperature at which a carbonyl-containing compound reacts with a hydroxylamine-containing compound to form an oxime-containing compound, where the decrease in temperature is relative to the reaction in the absence of the accelerant; (e) decrease the time necessary to react a carbonyl-containing compound with a hydroxylamine-containing compound to form an oxime-containing compound, wherein the decrease in time is relative to the reaction in the absence of accelerant; (f) decrease the amount of reagents necessary to form an oxime group on a non-natural amino acid polypeptide, wherein the decrease in amount of reagents is relative to the reaction in the absence of accelerant; (g) decrease the side products resulting from the reaction of a carbonyl-containing compound with a hydroxylamine-containing compound to form an oxime-containing compound, wherein the decrease in side products is relative to the reaction in the absence of accelerant; (h) does not irreversibly destroy the tertiary structure of a polypeptide undergoing an oxime-forming reaction in the presence of an accelerant (excepting, of course, where the purpose of the reaction is to destroy such tertiary structure); (i) can be separated from an oxime-containing compound in vacuo; and (j) modulate the reaction of a carbonyl-containing compound with a hydroxylamine-containing compound. In further embodiments, the accelerant has at least two of the aforementioned properties, three of the aforementioned properties, four of the aforementioned properties, five of the aforementioned properties, six of the aforementioned properties, seven of the aforementioned properties, eight of the aforementioned properties, nine of the aforementioned properties, or all of the aforementioned properties. In a further embodiment, the accelerant has none of the aforementioned properties.

The use of an accelerant includes the use of a single accelerant or multiple accelerants. In addition, the molar ratio of accelerant to carbonyl-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the molar ratio of accelerant to hydroxylamine-containing compound includes values between about 0.5:1 to 5000:1, including by way of example only 4000:1, 3000:1, 2000:1, 1000:1, 500:1, 400:1, 300:1, 200:1, 100:1, 50:1, 40:1, 30:1, 20:1, 10:1, 9:1, 8:1, 7:1, 6:1, 5:1, 4:1, 3:1, 2:1, 1:1, 0.9:1, 0.8:1, 0.7:1, 0.6:1, and 0.5:1. Further, the accelerant includes compounds that can be substantially removed in vacuo from the resulting oxime-containing compound. Further, the accelerant includes compounds containing a diamine moiety, a semicarbazide moiety, a hydrazine, or a hydrazide moiety.

Further, in any of the aforementioned aspects or embodiments, the accelerant is selected from the group consisting of bifunctional aromatic amines, oxoamine derivatives, and compounds having the following structures:

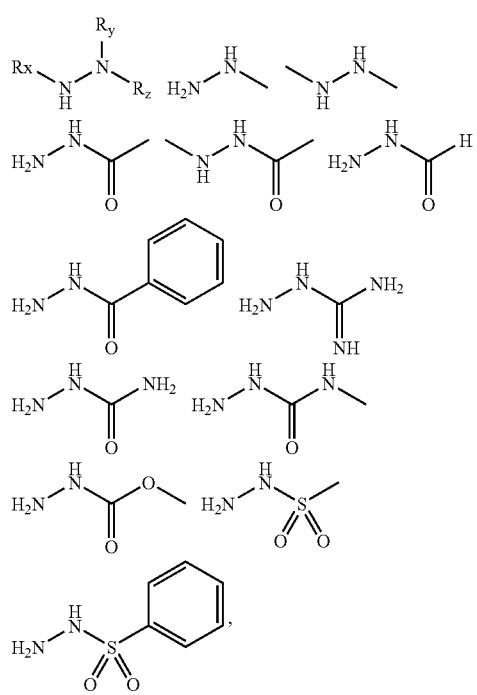

wherein $R_x$, $R_y$, and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, $SO_2$.

In a further embodiment, the accelerant is a bifunctional aromatic amine. In a further embodiment, the aromatic amine is selected from the group:

Bifuctional Aromatic Amines:

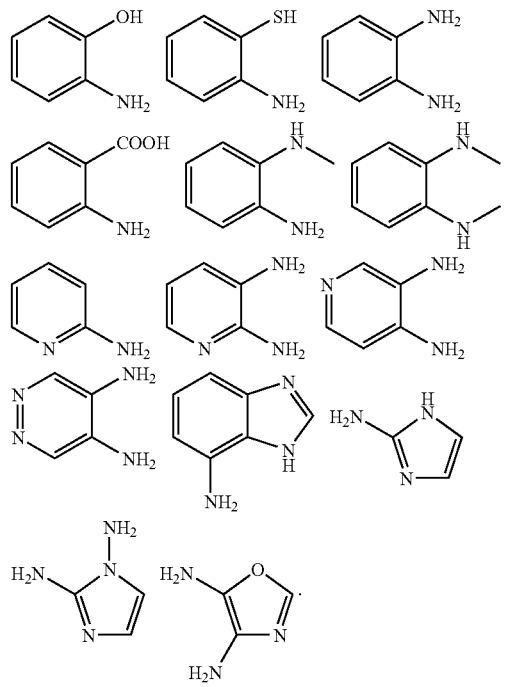

In a further embodiment, the accelerant is an oxoamine derivative. In a further embodiment, the oxoamine derivative is selected from the group:

Oxoamine Derivatives:

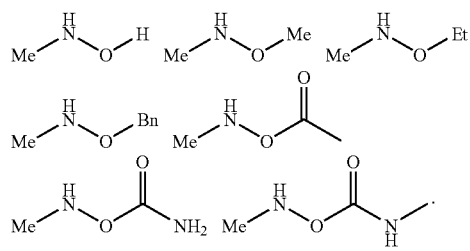

Further, the accelerant include compounds selected from the group consisting of:

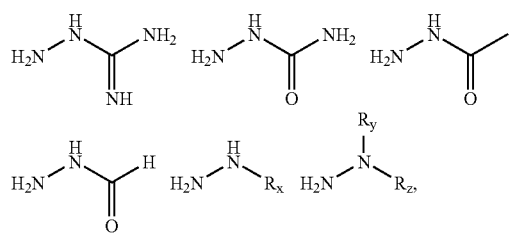

wherein $R_x$, $R_y$ and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), and C(=NH)—NH. Further, in any of the aforementioned aspects or embodiments, the accelerant is selected from the compounds presented in FIG. 5, FIG. 9, or FIG. 10, including by way of example any of compounds 6, 8, 10, 7, and 20 of FIG. 5. In any of the aforementioned aspects or embodiments, the accelerant includes an agent that can form a hydrazone upon reaction with a carbonyl-containing group. Further, in any of the aforementioned aspects the accelerant activity depends on the rate of reaction with the ketone moiety and the stability of the resulting intermediate. Further, in any of the aforementioned aspects or embodiments, the pH of the reaction mixture comprising the accelerant, the carbonyl-containing compound and the hydroxylamine-containing compound is between about 2.0 and 10; between about 2.0 and 9.0; between about 2.0 and 8.0; between about 3.0 and 7.0; between about 4.0 and 6.0; between about 3.0 and 10.0; between about 4.0 and 10.0; between about 3.0 and 9.0; between about 3.0 and 8.0; between about 2.0 and 7.0; between about 3.0 and 6.0; between about 4.0 and 9.0; between about 4.0 and 8.0; between about 4.0 and 7.0; between about 4.0 and 6.5; between about 4.5 and 6.5; about 4.0; about 4.5; about 5.0; about 5.5; about 6.0; about 6.5; and about 7.0.

Expression in Alternate Systems

Several strategies have been employed to introduce non-natural amino acids into proteins in non-recombinant host cells, mutagenized host cells, or in cell-free systems. These systems are also suitable for use in making the non-natural amino acid polypeptides described herein. Derivatization of amino acids with reactive side-chains such as Lys, Cys and Tyr resulted in the conversion of lysine to $N^2$-acetyl-lysine. Chemical synthesis also provides a straightforward method to incorporate non-natural amino acids. With the recent development of enzymatic ligation and native chemical ligation of peptide fragments, it is possible to make larger proteins. See, e.g., P. E. Dawson and S. B. H. Kent, *Annu. Rev. Biochem,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired non-natural amino acid is added to an in vitro extract capable of supporting protein biosynthesis, has been used to site-specifically incorporate over 100 non-natural amino acids into a variety of proteins of virtually any size. See, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of non-natural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111: 8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the non-natural amino acid analog. Induction of expression of the recombinant protein results in the accumulation of a protein containing the non-natural analog. For example, using this strategy, o, m and p-fluorophenylalanine have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskom, J. Kellermann and R Huber, *Eur. J. Biochem.,* 230:788 (1995); and, N. Budisa, W. Kambrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Hest and D. A. Tirrell *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, Tetrahedron, 56:9487 (2000); U.S. Pat. No. 6,586, 207; U.S. Patent Publication 2002/0042097, which are incorporated by reference herein.

The success of this method depends on the recognition of the non-natural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.,* 275: 40324 (2000).

Another strategy to incorporate non-natural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, Science, 292:501 (2001). ValRS can misaminoacylate tRNAVal with Cys, Thr, or aminobutyrate (Abu); these non-cognate amino acids are subsequently hydrolyzed by the editing domain. After random mutagenesis of the Escherichia coli chromosome, a mutant Escherichia coli strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant Escherichia coli strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing non-natural amino acids. For example, see the following publications and references cited within, which are as follows: Crick, F. H. C., Barrett, L. Brenner, S. Watts-Tobin, R. *General nature of the genetic code for proteins. Nature,* 192:1227-1232 (1961); Hofmann, K., Bohn, H. *Studies on polypeptides. XXXVI. The effect of pyrazole-imidazole replacements on the S-protein activating potency of an S-peptide fragment, J. Am Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Non-natural Catalytic Residues, Science,* 266(5183): 243 (1994).

Chemical modification has been used to introduce a variety of non-natural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enzyme active sites, Science,* 226 (4674):505-511 (1984); Neet, K. E., Nanci A, Koshland, D. E. *Properties of thiol-subtilisin, J Biol. Chem,* 243(24):6392-6401 (1968); Polgar, L. et M. L. Bender. *A new enzyme containing a synthetically formed active site. Thiol-subtilisin. J. Am Chem Soc,* 88:3153-3154 (1966); and, Pollack, S. J., Nakayama, G. Schultz, P. G. *Introduction of nucleophiles and spectroscopic probes into antibody combining sites, Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that non-natural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of non-natural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing non-natural amino acids site-specifically into proteins, Methods in Enz., vol.* 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

The following patents are incorporated by reference in their entirety for in vivo methods for incorporating non-natural amino acids into proteins and other polypeptides, and for methods for producing the appropriate synthetases/tRNAs: U.S. Pat. Nos. 7,045,337 and 7,083,970.

For example, a suppressor tRNA was prepared that recognized the stop codon UAG and was chemically aminoacylated with an non-natural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res,* 16(3):791-802 (1988). When the acylated suppressor tRNA and the mutant gene were combined in an in vitro transcription/translation system, the non-natural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded potential catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-natural amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which is incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), to avoid the use of synthetases in aminoacylation. Such methods or other chemical aminoacylation methods may be used to aminoacylate tRNA molecules described herein.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{C-CCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Aminoacylate tRNAs ribozymes can be immobilized on a substrate so as to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs described herein may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-natural amino acids into proteins. Lu et al. in Mol Cell. 2001 October; 8(4):759-69 describe a method in which a protein is chemically ligated to a synthetic peptide containing non-natural amino acids (expressed protein ligation).

Microinjection techniques have also been use incorporate non-natural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science,* 268:439 (1995); and, D. A. Dougherty, *Curr. Opin. Chem. Biol.,* 4:645 (2000). A Xenopus oocyte was coinjected with two RNA species made in vitro: an mRNA encoding the target protein with a UAG stop codon at the amino acid position of interest and an amber suppressor tRNA aminoacylated with the desired non-natural amino acid. The translational machinery of the oocyte then inserts the non-natural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271:19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

The ability to incorporate non-natural amino acids directly into proteins in vivo offers a wide variety of advantages, including by way of example only, high yields of mutant proteins, technical ease, the potential to study the mutant proteins in cells or possibly in living organisms and the use of these mutant proteins in therapeutic treatments and diagnostic uses. The ability to include non-natural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.,* 7:419 (1998).

It may also be possible to obtain expression of a non-natural amino acid polypeptide described herein using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukatyotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering,* 74 :309-316 (2001); Kim, D. M. and J. R. Swartz, *Biotechnology Letters,* 22, 1537-1542, (2000); Kim, D. M., and J. R. Swartz, *Biotechnology Progress,* 16, 385-390, (2000); Kim, D. M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of non-natural amino acid polypeptides includes the mRNA-peptide fusion technique. See, e.g., R. Roberts and J. Szostak, *Proc. Natl Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of non-natural amino acid polypeptides comprising one or more non-natural amino acids to identify polypeptides having desired properties. More recently, in vitro ribosome translations with purified components have been reported that permit the synthesis of peptides substituted with non-natural amino acids. See, e.g., A. Forster et al., *Proc. Natl Acad. Sci. (USA)* 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

EXAMPLES

Example 1

Improved Oxime Formation in the Presence of Accelerant

A carbonyl-containing compound (non-natural amino acid polypeptide) is shown in Scheme 1A. The keto group of the amino acid para-acetylphenylalanine incorporated into the protein reacts with a hydroxylamine-containing compound to form a relatively stable oxime. This reaction is highly specific. A faster reaction was observed in the presence of an accelerant (Scheme 1B).

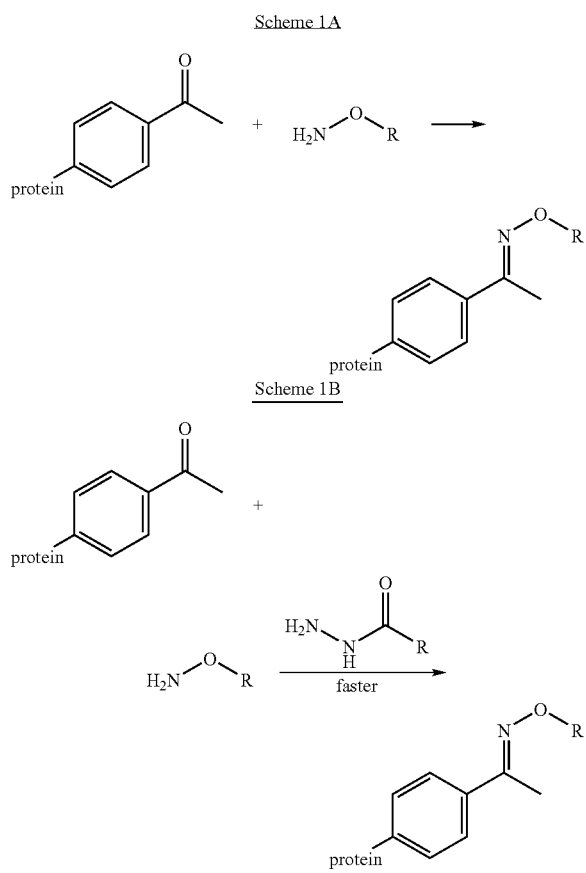

Example 2

Screening of Potential Accelerants Using 30 K PEG hGH-pAcF Conjugation

Figure 5:
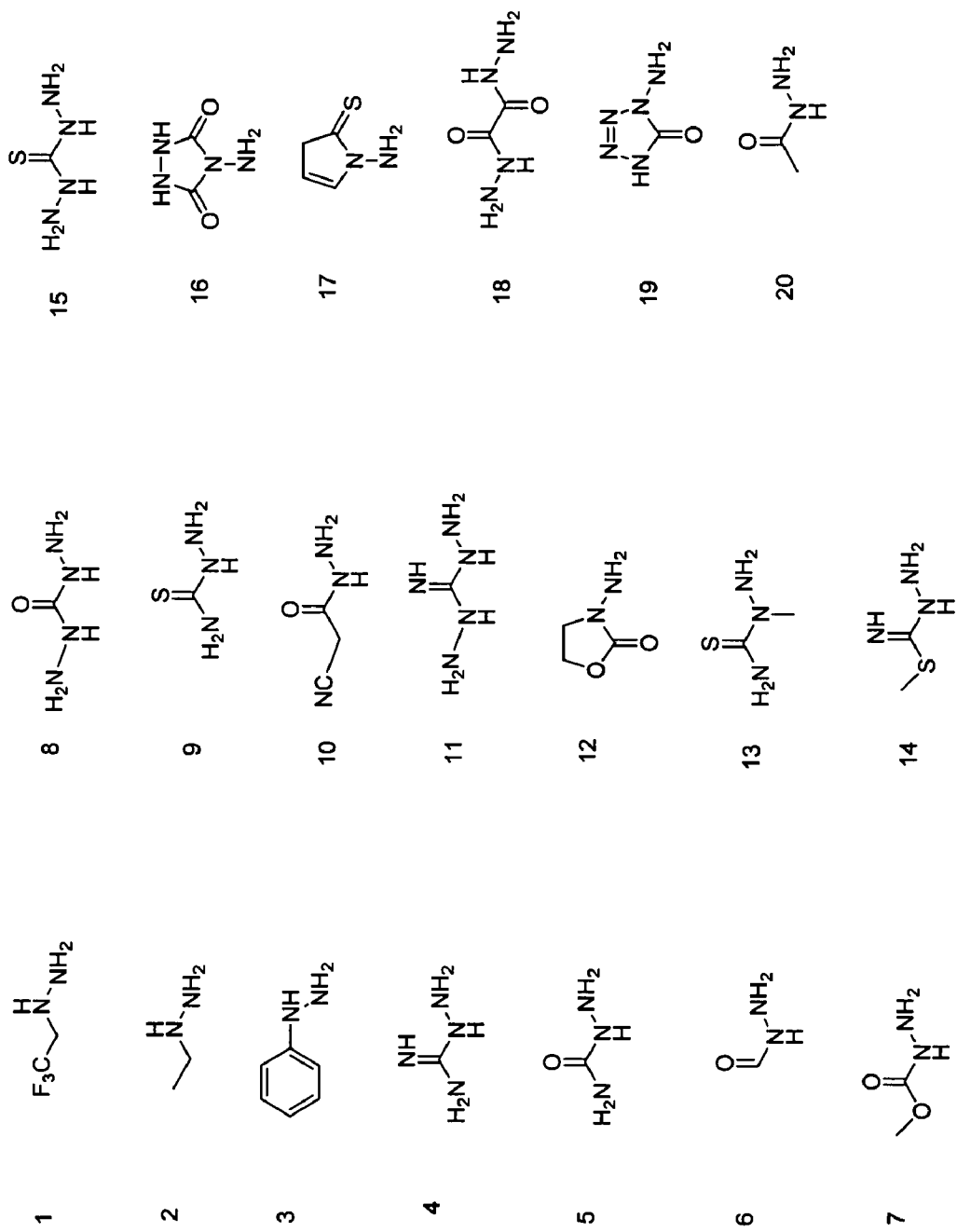
FIG. 5 presents non-limiting examples of accelerants that can be used in the methods, reactions and syntheses described herein.
Figure 6:
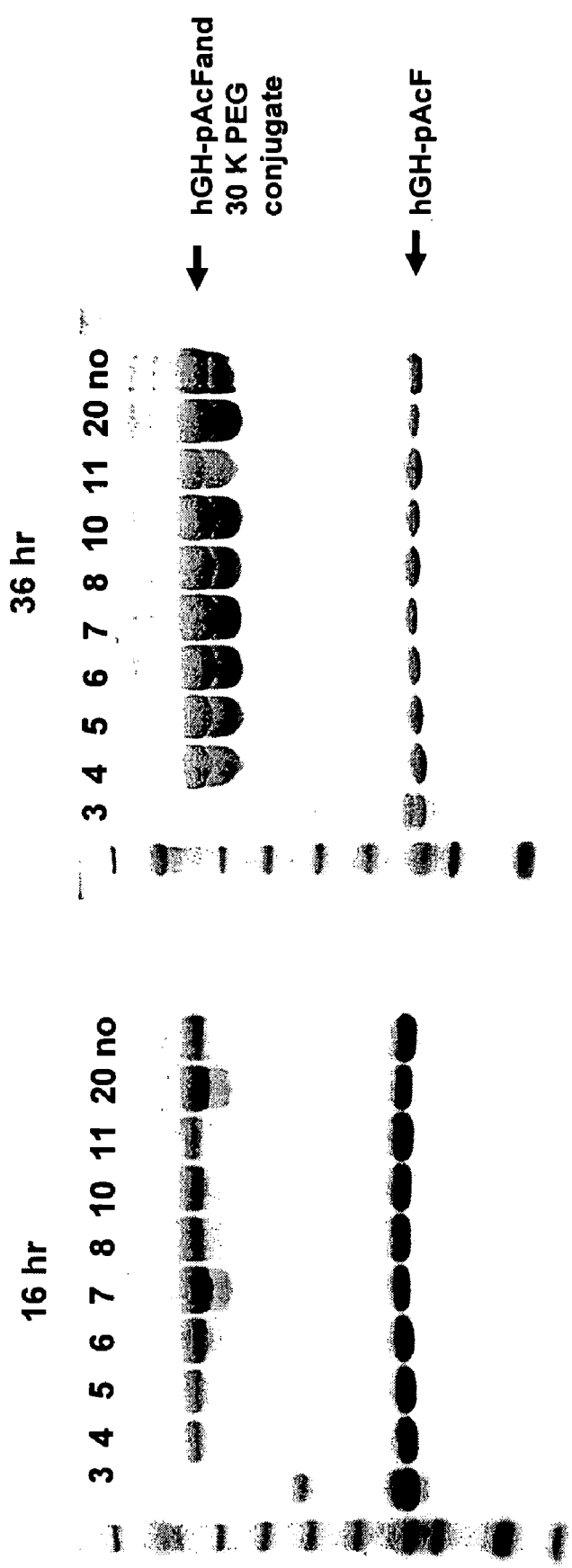
FIG. 6 presents a non-limiting example of an SDS-PAGE analysis comparing the formation of oxime in the presence of different accelerants; the lane number corresponds to the accelerant number in FIG. 5 and the last lane is a control reaction without accelerant.
Figure 7:
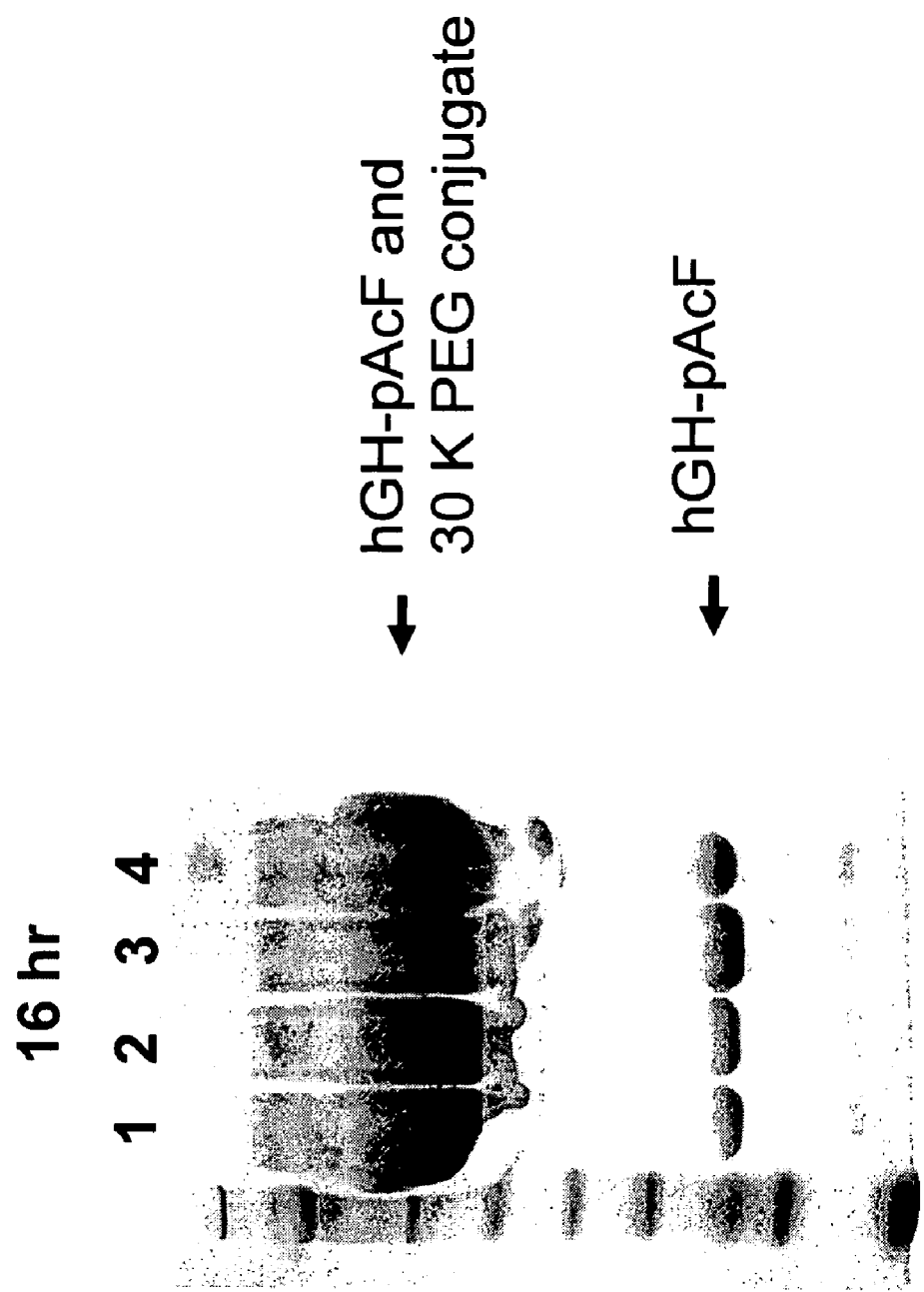
FIG. 7 presents a non-limiting example of an SDS-PAGE analysis of the conjugation of hGH-pAcF with 30 K monohydroxylamine PEG with accelerants 7 and 20:1) hGH-pAcF:PEG=1:2 with accelerant 7; 2) hGH-pAcF PEG=1:2 with accelerant 20; 3) hGH-pAcF:PEG=1:2 no accelerant; 4) hGH-pAcF:PEG=1:5 no accelerant.

Human growth hormone (hGH) with para-acetylphenylalanine substituted for tyrosine at position 35 was used to screen a panel of 20 compounds (FIG. 5). hGH was buffer exchanged into hGH reaction buffer (20 mM NaOAc, 20 mg/ml glycine, 5 mg/ml Mannitol, 1 mM EDTA, pH 4.0) using a PD 10 column, and concentrated to 10 mg/ml using a Centrocon (10 K MWCO) concentrator. hGH (10 μl) was mixed with 3.6 μl mono hydroxylamine 30 K PEG (2.5 mM), 3 μl of potential accelerant solution (200 mM in hGH reaction buffer) and buffer to give a final volume of 30 μl. The molar ratio of hGH:PEG was 1:2. The reaction mixtures were incubated at 28° C. for 16 hours and 36 hours and analyzed by SDS-PAGE (FIG. 6). Each lane of the gels shown in FIG. 6 is labeled with the compound tested as shown in FIG. 5. The last lane in each gel was a control reaction (no accelerant). Compounds 6, 7, 8, 10, and 20 were accelerants. Two compounds from the panel, compounds 7 and 20 (acetic hydrazide) (pictured in FIG. 5), were accelerants and were further evaluated under similar reaction conditions with a higher hGH protein concentration (8 mg/ml). The reaction mixtures were incubated at 28° C. for 16 hours, and the results from SDS-PAGE analysis are shown in FIG. 7. Lane 1 was a reaction mixture with a hGH:PEG molar ratio of 1:2 and 50 mM of accelerant compound 7. Lane 2 was a reaction mixture with a hGH:PEG molar ratio of 1:2 and 50 mM of accelerant compound 20. Lane 3 was a reaction mixture with a hGH:PEG molar ratio of 1:2 with no accelerant. Lane 4 was a reaction mixture with a hGH:PEG molar ratio of 1:5 with no accelerant. After 16 hours, both compounds were shown to catalyze the reaction.

Example 3

LCMS Analysis of hGH After Incubation with Accelerant

Figure 8A:
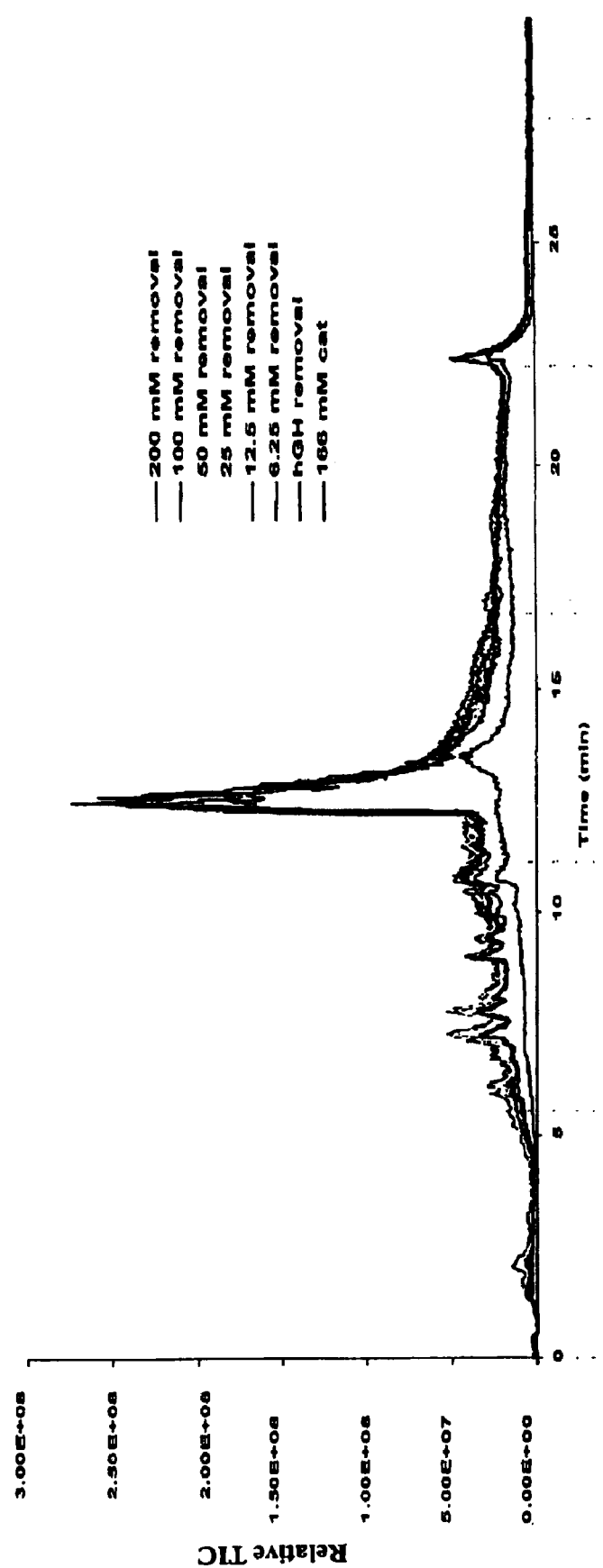
FIG. 8 presents a non-limiting example of an LCMS analysis of hGH incubated with different concentrations of accelerant acetic hydrazide: A) total LCMS trace; B) Mass spectrum of hGH without accelerant; C) Mass spectrum of hGH with 200 mM accelerant acetic hydrazide.
Figure 8B:
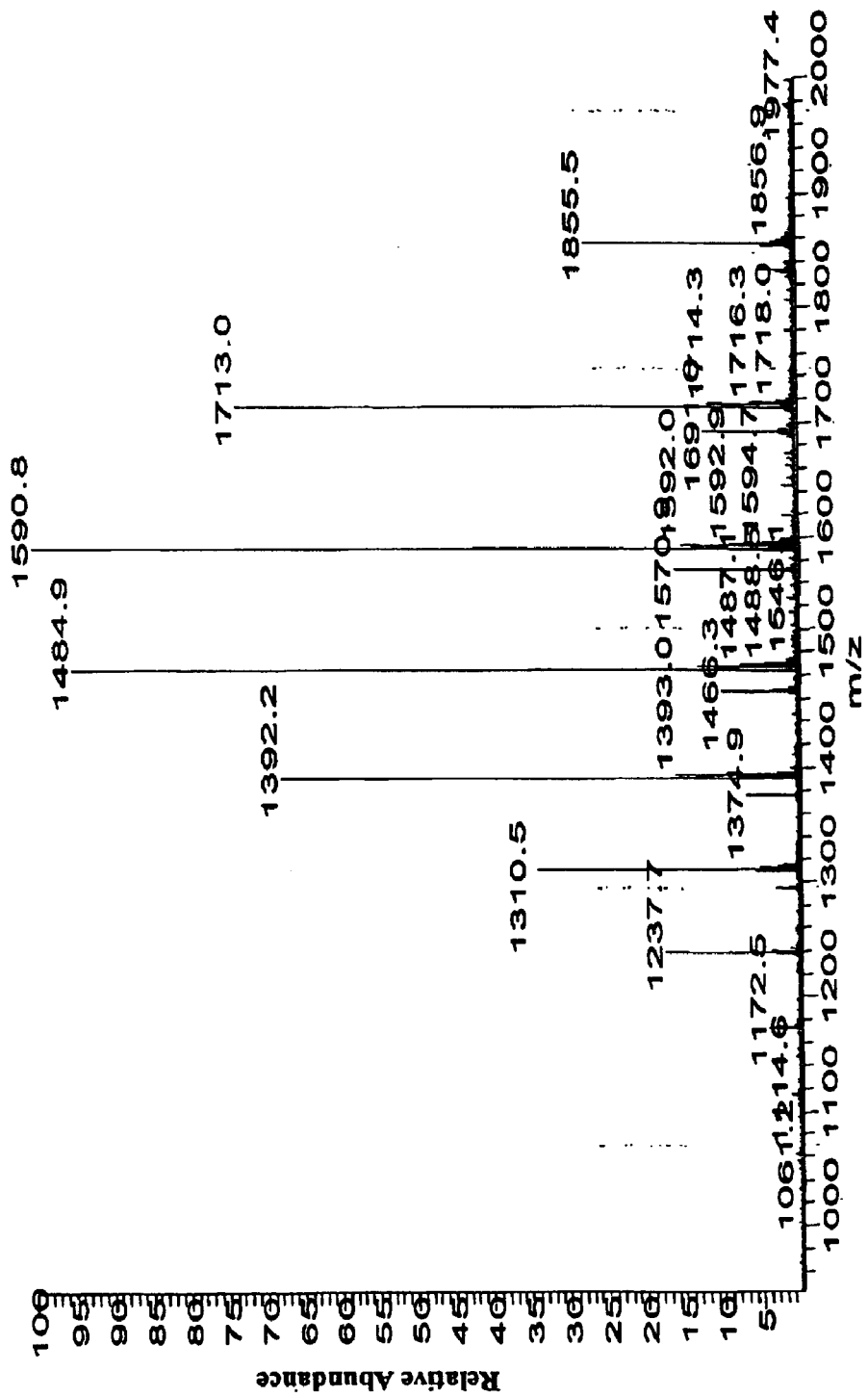
Figure 8C:
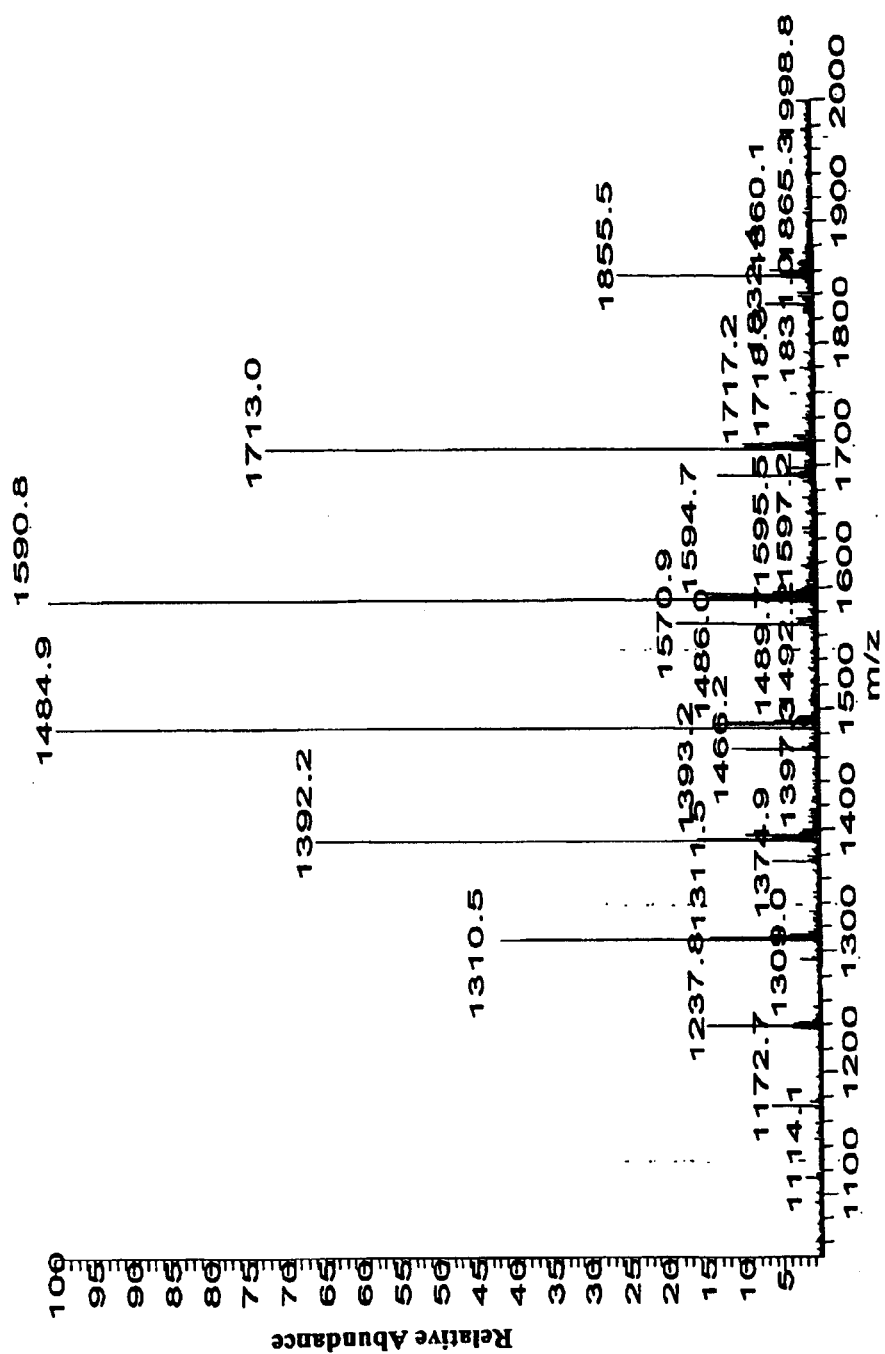

In hGH reaction buffer, wild type hGH (5.8 mg/ml) was incubated with various concentrations of the accelerant acetic hydrazide (200 mM, 100 mM, 50 mM, 25 mM, 12.5 mM, 6.25 mM and 0 mM) at 28° C. for 48 hours. The accelerant was removed through dialysis (10 k MWCO). The resulting protein solutions were analyzed by LCMS (FIG. 8).] FIG. 10A shows the total LCMS trace. FIG. 8B shows the mass spectrum of hGH without accelerant. FIG. 8C shows the mass spectrum of hGH with 200 mM accelerant acetic hydrazide.

An accelerant for protein conjugation preferably does not exert any deteriorative effects on protein, such as fragmentation, precipitation, and undesired covalent modification. No fragmentation was observed when using accelerants 7 and 20 (shown in FIG. 5) based on SDS-PAGE analysis and protein precipitation in all the conditions used with both scFv and hGH. For example, no covalent modification could be detected with LCMS after 48 hour of incubation of wild type hGH with up to 200 mM accelerant 20 (acetic hydrazide). The measured molecular weights of hGH in all the conditions are same and match theoretical value 22256.

Example 4

One Step Dimerization of scFv-pAcF

Figure 2:
FIG. 2 presents a non-limiting example of a SDS-PAGE analysis of one step dimerization reactions of scFv 108 using 2 K homobifunctional hydroxylamine PEG linker with different molar ratios: 1) scFv:linker=1.6:1, with acetic hydrazide; 2) scFv:linker=2:1, with acetic hydrazide; 3) scFv:linker=2.4:1, with acetic hydrazide; 4) scFv:linker=2:1, without acetic hydrazide; 5) scFv:linker=2:1, with acetic hydrazide without PEG linker.

Single chain Fv (scFv) 108 protein with para-acetylphenylalanine substituted at position 259 (scFv 108 259-pAcF) was used the following conjugation experiment. scFv 108 259-pAcF in storage buffer was buffer exchanged into reaction buffer (150 mM NaCl, 20 mM NaOAc, 5 mM EDTA, pH 4.0) using a PD 10 column. The protein solution was concentrated to 0.5 mM, mixed with hydroxylamine homobifunctional 2 K PEG linker 2.5 mM stock solution and supplemented with acetic hydrazide as accelerant. The final reaction mixture consisted of 147 μM homobifunctional 2 K PEG linker, the corresponding concentration of pAcF-substituted scFv and 47 mM acetic hydrazide. The reaction mixtures were incubated at 28° C. and analyzed at different time points (6 hours, 20 hours, 44 hours) by SDS-PAGE (FIG. 2).

To make the one-step reaction more efficient and more practical with the homobifunctional 2 K PEG linker, accelerants were used to facilitate the dimerization process. Without accelerant, very little dimer product could be detected after 20 hours by SDS-PAGE. Lane 4 of the 6 hour, 20 hour, and 44 hour gels show reaction mixtures with a scFv:PEG linker molar ratio of 2.0:1 without the accelerant acetic hydrazide. On the other hand, in the presence of 47 mM acetic hydrazide, the dimer product appeared after 6 hours. As shown in FIG. 2, different protein and linker molar ratios, 1.6:1, 2.0:1 and 2.4:1, were tested to scan for the best conjugation conditions. Lane 1 of the 6 hour, 20 hour, and 44 hour gels show reaction mixtures with a scFv:PEG linker molar ratio of 1.6:1 with acetic hydrazide. Lane 2 of the 6 hour, 20 hour, and 44 hour gels show reaction mixtures with a scFv:linker molar ratio of 2.0:1 with acetic hydrazide. Lane 3 of the 6 hour, 20 hour, and 44 hour gels show reaction mixtures with a scFv:linker molar ratio of 2.4:1 with acetic hydrazide. As a control, scFv 108 was incubated with 47 mM acetic hydrazide in the absence of the homobifunctional PEG linker for 44 hours. No dimer formation was observed. Lane 5 of the 6 hour, 20 hour, and 44 hours gels show reaction mixtures of scFv and accelerant acetic hydrazide without the PEG linker. This result indicates that the accelerant, acetic hydrazide, does not facilitate the formation of intermolecular disulfide bonds among scFv. In the presence of homobifunctional PEG linker, the dimer is produced through the oxime formation between the PEG linker and protein.

Example 5

Figure 3:
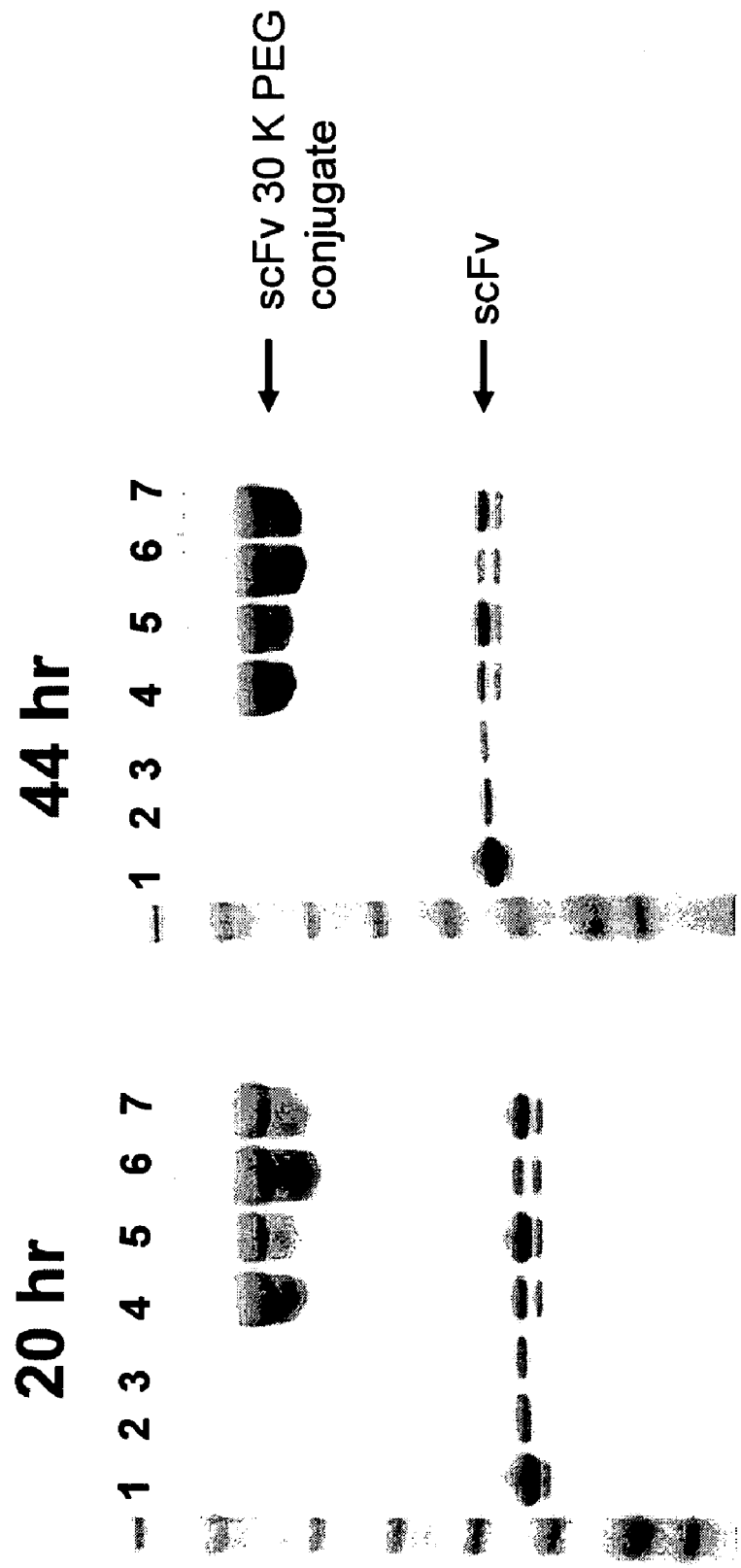
FIG. 3 presents a non-limiting example of a SDS-PAGE analysis of scFv-pAcF and 30 K mono hydroxylamine PEG conjugation 1) the standard of 100% starting scFv-pAcF; 2) the standard of 20% starting scFv-pAcF; 3) the standard of 10% starting scFv-pAcF; 4) scFv:PEG=1:3 with 20 mM acetic hydrazide; 5) scFv:PEG=1:3 without acetic hydrazide; 6) scFv:PEG=1:5 with 20 mM acetic hydrazide; 7) scFv:PEG=1:5 without acetic hydrazide.

Mono Hydroxylamine 30 K PEG and scFv-pAcF Conjugation scFv 108 259-pAcF 0.5 mM stock solution in reaction buffer mentioned above (10 μl) is mixed with various amounts of mono hydroxylamine 30 K PEG 2.5 mM stock solution, 2.2 μl of 200 mM acetic hydrazide stock solution and reaction buffer. The reaction mixtures with a final reaction volume of 22 μl have different molar ratios of scFv:PEG (1:3 or 1:5). The accelerating effect of acetic hydrazide on conjugation of mono hydroxylamine 30 K PEG and scFv was evaluated at protein and PEG molar ratio of 1:3 and 1:5 with and without accelerant. The reaction mixtures were incubated at 28° C. and were analyzed at different time points (20 hours, 44 hours) by SDS-PAGE (FIG. 3). Lanes 1, 2, and 3 show 100%, 20%, and 10% of the starting scFv-pAcF, respectively. Lane 4 of the 20 hour and 44 hour gels show reaction mixtures with a scFv:PEG molar ratio of 1:3 with 20 mM acetic hydrazide. Lane 5 of the 20 hour and 44 hour gels show reaction mixtures with a scFv:PEG molar ratio of 1:3 without accelerant Lane 6 of the 20 hour and 44 hour gels show reaction mixtures with a scFv:PEG molar ratio of 1:5 with 20 mM acetic hydrazide. Lane 7 of the 20 hour and 44 hour gels show reaction mixtures with a scFv:PEG molar ratio of 1:5 without accelerant. The conjugation results demonstrated that acetic hydrazide accelerates the conjugation reaction. The reaction at a 1:3 molar ratio of protein:PEG with accelerant proceeded faster than the reaction at a 1:5 ratio of protein:PEG without accelerant.

Figure 4:
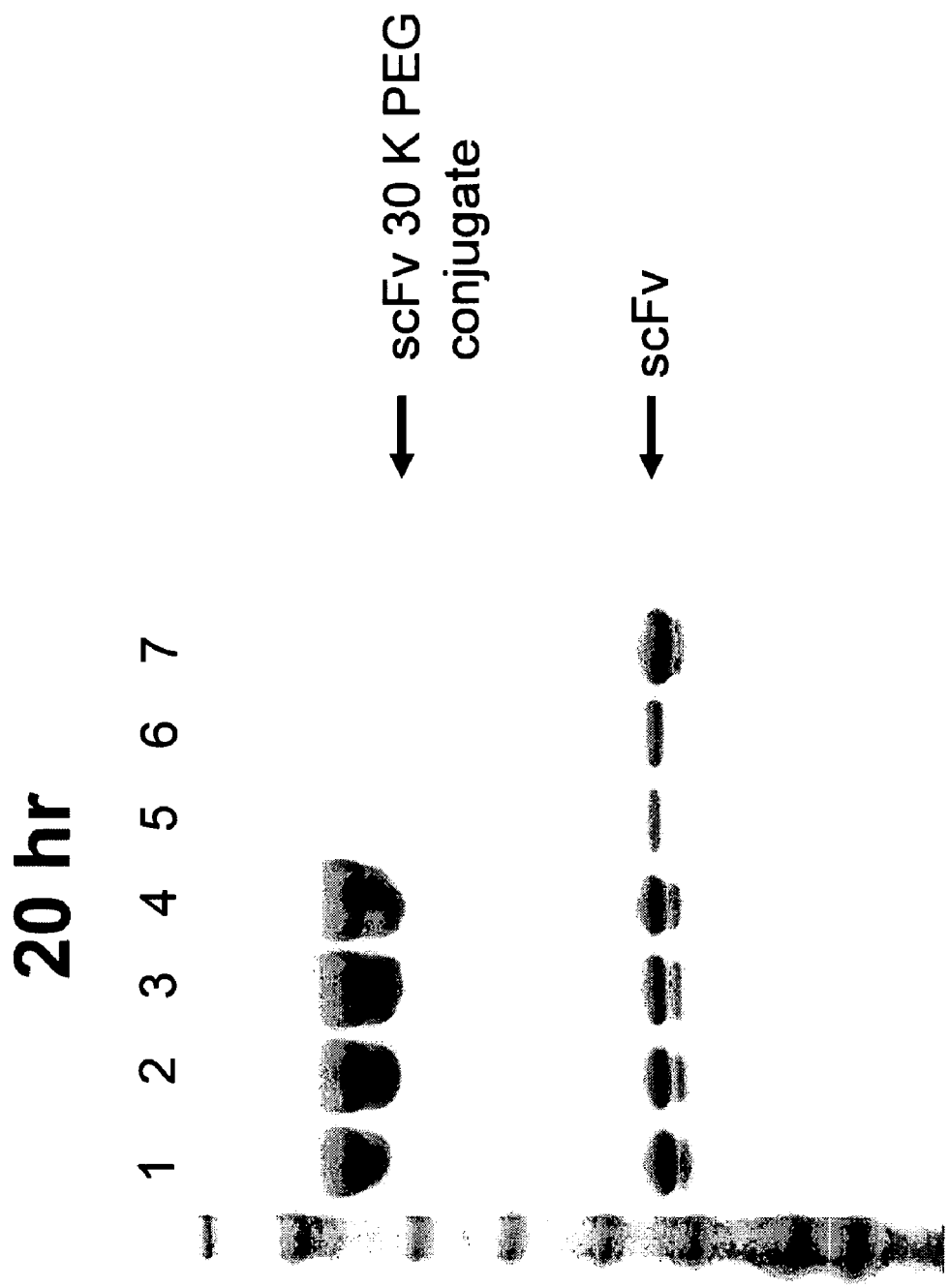
FIG. 4 presents a non-limiting example of a SDS-PAGE analysis of scFv-pAcF and 30 K mono hydroxylamine PEG conjugation with different concentration of acetic hydrazide. 1) scFv-pAcF:PEG=1:2, 5 mM acetic hydrazide; 2) scFv-pAcF:PEG=1:2, 20 mM acetic hydrazide; 3) scFv-pAcF:PEG 1:2, 80 mM acetic hydrazide; 4) scFv-pAcF:PEG=1:5, no acetic hydrazide; 5) the standard of 10% scFv-pAcF; 6) the standard of 20% scFv-pAcF; 7) the standard of 100% scFv-pAcF.

Similarly, the relative conjugation efficiency of different concentrations of the accelerant acetic hydrazide (5 mM, 20 mM, 80 mM) with a scFv:30 K PEG mono hydroxylamine molar ratio of 1:2 were evaluated (FIG. 4). The reaction mixtures were incubated at 28° C. Lane 1 shows the reaction mixture with 5 mM acetic hydrazide (scFv:30 K PEG mono hydroxylamine molar ratio of 1:2). Lane 2 shows the reaction mixture with 20 mM acetic hydrazide (scFv:30 K PEG mono hydroxylamine molar ratio of 1:2). Lane 3 shows the reaction mixture with 80 mM acetic hydrazide (scFv:30 K PEG mono hydroxylamine molar ratio of 1:2). Lane 4 shows the reaction mixture with no acetic hydrazide (scFv:30 K PEG mono hydroxylamine molar ratio of 1:5). Lanes 5, 6, and 7 show 10%, 20%, and 100% of the starting scFv-pAcF, respectively. SDS-PAGE analysis showed that the higher concentration of accelerant, the faster the conjugation. The conjugation at a scFv:PEG molar ratio of 1:2 in the presence of 80 mM accelerant is faster than the conjugation at a scFv:PEG molar ratio of 1:5 without the accelerant.

Example 6

Small Molecule Studies of Accelerated Oxime Formation

Figure 11:
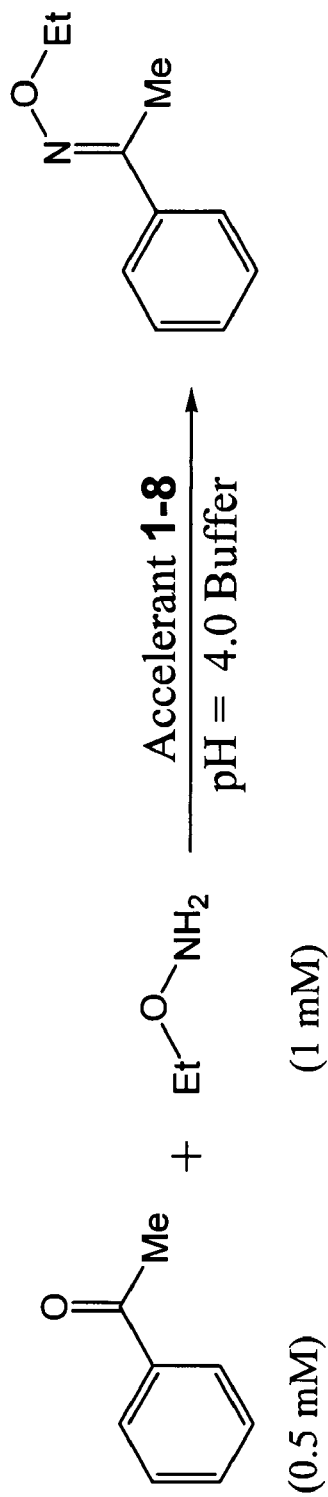
FIG. 11 presents a non-limiting set of oxime yields for a model reaction conducted in the absence and in the presence of various accelerants described herein.

Acetophenone (0.5 mM) was reacted with ethylhydroxylamine (1 mM) in aqueous solution buffered to a pH of about 4.0; a series of accelerants (20 mM) was added to this reaction mixture to determine the effect of accelerant identity on the rate and yield of oxime formation (see FIG. 10(a)). The accelerants that were tested in this model reaction are presented in FIG. 10(b). Aliquots were taken from the reaction mixture and analyzed by high-performance liquid chromatography after 2 h, 5 h, 9 h, and 24 h. In addition, for each of these samples, the ketone peak absorbance was compared to the oxime peak absorbance at 260 nm using UV/V is spectroscopy. FIG. 11 presents the results after 2 h and 9 h of reaction. As can be seen, all accelerants increase the rate of oxime formation; however, accelerants 1 and 7 (shown in FIG. 10(b)) provide the highest yield, with accelerant 1 providing the highest yield following longer reaction times. Without being bound to a particular theory, the activity of the accelerant appears to depend on both the rate of reaction with the ketone and on the stability of the hydrazone intermediate.

It is understood that the examples and embodiments described herein are for illustrative purposes only and that various modifications or changes in light thereof will be suggested to persons of ordinary skill in the art and are to be included within the spirit and purview of this application and scope of the appended claims. All publications, patents, and patent applications cited herein are hereby incorporated by reference in their entirety for all purposes.

What is claimed is:

1. A reaction mixture comprising a compound comprising an aromatic ketone moiety, a compound comprising a hydroxylamine moiety, and an accelerant selecting from the group consisting of bifunctional aromatic amines, oxoamine derivatives, and compounds having the following structures:

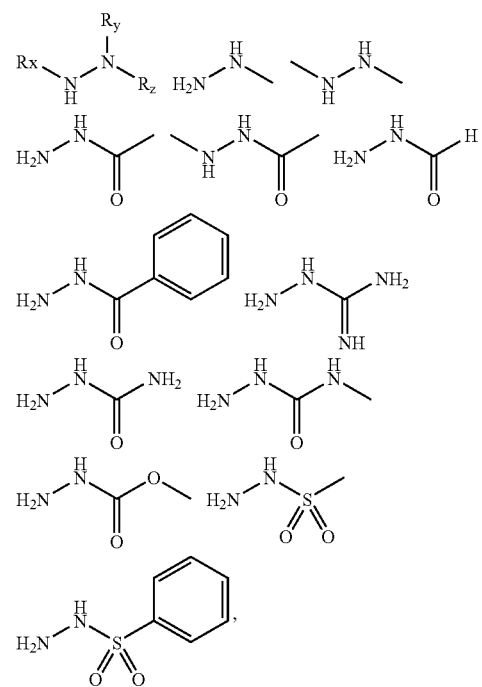

wherein $R_x$, $R_y$, and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH, SO, and $SO_2$.

2. The reaction mixture of claim 1, wherein the compound comprising an aromatic ketone moiety is an amino acid or a polypeptide.

3. The reaction mixture of claim 1, wherein the compound comprising an aromatic ketone moiety has the structure:

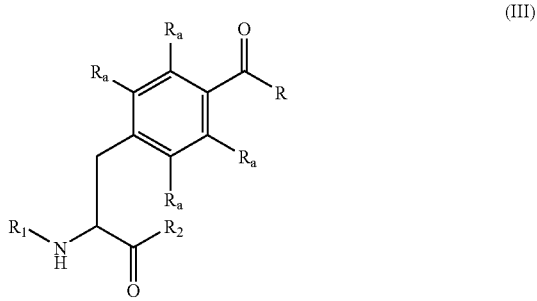

(III)

wherein:
R is alkyl substituted alkyl cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

4. The reaction mixture of claim 1, wherein the compound comprising a hydroxylamine moiety further comprises a polymer moiety.

5. The reaction mixture of claim 1, wherein the compound comprising a hydroxylamine moiety has the structure:

(XXVII)

wherein:
each L is a linker independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl.

6. The reaction mixture of claim 1, wherein the accelerant is a bifunctional aromatic amine.

7. The reaction mixture of claim 1, wherein the accelerant is an oxoamine derivative.

8. A method for derivatizing an amino acid of Formula (III), the method comprising contacting the amino acid with a reagent of Formula (XXVII) in the presence of an accelerant, wherein Formula (III) corresponds to:

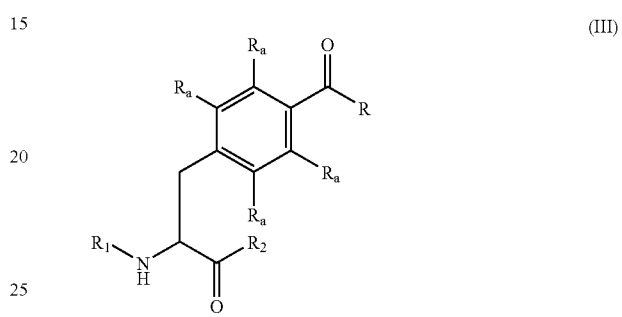

(III)

wherein:
R is alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R',
wherein Formula (XXVII) corresponds to:

(XXVII)

wherein:
each L is a linker independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N=, —C(R')=N—, —C(R')=N—N(R')—, —C(R')=N—N=, —C(R')$_2$—

N=N—, and —C(R')₂—N(R')—N(R')—, where each R' is independently H, alkyl, or substituted alkyl; and wherein the accelerant is selected from the group consisting of bifunctional aromatic amines, oxoamine derivatives, and compounds having the following structures:

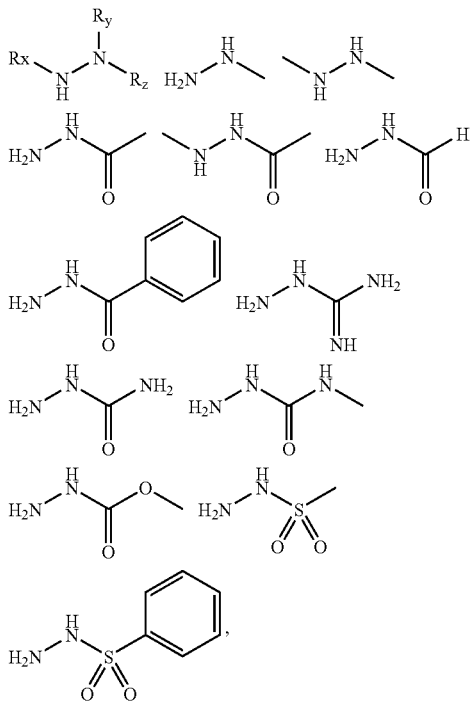

wherein $R_x$, $R_y$, and $R_z$ are selected from the group consisting of: $L_x$-H, $L_x$-alkyl, $L_x$-aryl, $L_x$-heteroaryl, $L_x$-alkenyl, $L_x$-alkynyl, $L_x$-alkoxy, and $L_x$-alkylamine, where $L_x$ is a bond, C(=O), C(=NH), C(=NH)—NH and SO, SO₂.

9. The method of claim 8, wherein R is alkyl.

10. The method of claim 8, wherein R is CH₃.

11. The method of claim 8, wherein the accelerant has the structure: H₂N—NH—C(O)—$R_b$, wherein $R_b$ is alkyl, substituted alkyl, NH—NH₂, H, and alkoxy.

12. The method of claim 11, wherein $R_b$ is alkyl or alkoxy.

13. The method of claim 8, wherein the accelerant is selected from the group consisting of

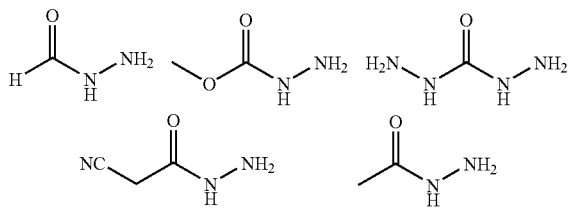

14. The method of claim 8, wherein the accelerant is a bifunctional aromatic amine.

15. The method of claim 14, wherein the bifunctional aromatic amine is selected from the group consisting of:

Bifuctional aromatic amines:

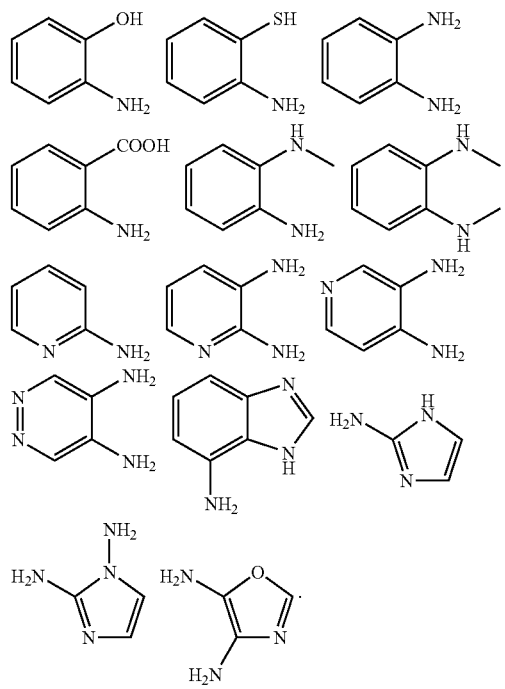

16. The method of claim 8, wherein the accelerant is an oxoamine derivative.

17. The method of claim 16, wherein the oxoamine is selected from the group consisting of:

Oxoamine derivatives:

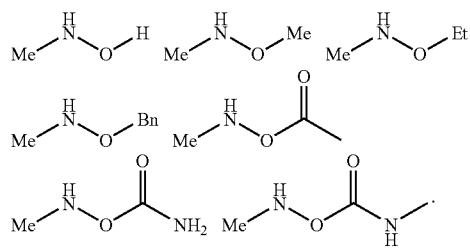

18. The method of claim 8, wherein the molecular weight of the PEG group is between about 1,000 Da and about 40,000 Da.

19. The method of claim 8, wherein the amino acid is contacted with the reagent of Formula (XXVII) in aqueous solution at about room temperature.

20. The method of claim 8, wherein the amino acid is contacted with the reagent of Formula (XXVII) in aqueous solution at a pH between about 4 to about 10.

21. The method of claim 8, wherein the molar ratio of amino acid to the reagent of Formula (XXVII) is selected from the group of about 1:2; 1:1; 1.5:1; 1.5:2; 2:1; 1:1.5; 2:1.5; and 1.5 to 2.

22. The method of claim 8, wherein the amino acid of Formula (III) has been incorporated site-specifically during the in vivo translation of a polypeptide.

23. The method of claim 8, wherein the derivatized amino acid comprises at least one oxime containing amino acid having the structure of Formula (XI-A):

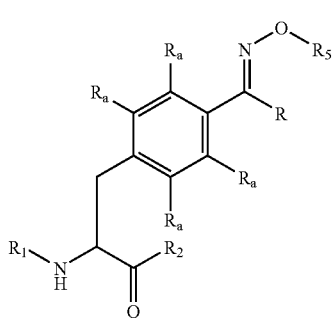

(XI-A)

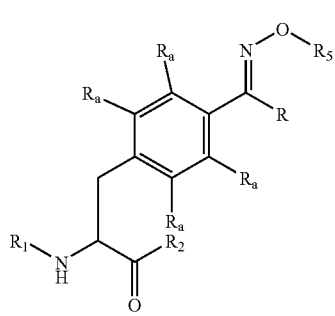

(XI-A)

wherein:
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R',
$R_5$ is L-X, where
X is a PEG; and
L is optional, and when present is a linker selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl.

24. A derivatized amino acid that comprises at least one oxime containing amino acid having the structure of Formula (XI-A):

wherein:
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R',
$R_5$ is L-X, where
X is a PEG; and
L is optional, and when present is a linker selected from the group consisting of alkylene, substituted alkylene, alkenylene, substituted alkenylene, —O—, —O-(alkylene or substituted alkylene)-, —S—S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl.

25. The derivatized amino acid of claim 24, wherein the amino acid is incorporated into a therapeutic protein that is a member of the growth hormone supergene family.

26. The derivatized amino acid of claim 25, wherein the therapeutic protein is human growth hormone.

* * * * *

UNITED STATES PATENT AND TRADEMARK OFFICE
CERTIFICATE OF CORRECTION

PATENT NO.         : 7,468,458 B2  
APPLICATION NO.    : 11/875761  
DATED              : December 23, 2008  
INVENTOR(S)        : Feng Tian and Zhenwei Miao Page 1 of 1

It is certified that error appears in the above-identified patent and that said Letters Patent is hereby corrected as shown below:

Title Page, Item (73) should read  
--(73) Assignee: Ambrx, Inc., La Jolla, CA (US)--

Signed and Sealed this

Tenth Day of March, 2009

JOHN DOLL  
*Acting Director of the United States Patent and Trademark Office*